United States Patent [19]
Misslitz et al.

[11] Patent Number: 5,514,642
[45] Date of Patent: May 7, 1996

[54] CYCLOHEXENONE OXIME ETHERS, THEIR PREPARATION AND THEIR USE

[75] Inventors: Ulf Misslitz, Neustadt; Norbert Meyer, Ladenberg; Juergen Kast, Boehl-Iggelheim; Dieter Kolassa, Limburgerhof; Helmut Walter, Obrigheim; Karl-Otto Westphalen, Speyer; Matthias Gerber, Limburgerhof; Uwe Kardorff, Mannhein, all of Germany

[73] Assignee: BASF Aktiengesellschaft, Ludwigshafen, Germany

[21] Appl. No.: 381,915

[22] PCT Filed: Aug. 13, 1993

[86] PCT No.: PCT/EP93/02158

§ 371 Date: Feb. 13, 1995

§ 102(e) Date: Feb. 13, 1995

[87] PCT Pub. No.: WO94/04489

PCT Pub. Date: Mar. 3, 1994

[30] Foreign Application Priority Data

Aug. 22, 1992 [DE] Germany ............... 42 27 896.1

[51] Int. Cl.$^6$ ............... C07D 213/04; C07D 309/04; A01N 43/16; A01N 43/18
[52] U.S. Cl. ............... 504/244; 504/193; 504/251; 504/254; 504/260; 504/285; 504/289; 504/294; 504/295; 504/290; 504/288; 504/292; 504/310; 504/315; 504/318; 504/322; 504/326; 504/337; 504/339; 504/344; 546/14; 546/200; 546/283; 546/284; 548/110; 548/247; 548/405; 548/517
[58] Field of Search ............... 504/288, 292, 504/244, 251, 254, 260, 283, 289, 294, 295, 290, 310, 315, 318, 322, 326, 337, 339, 344, 193; 546/200, 283, 284, 14; 548/110, 517, 527, 531, 543, 558, 561, 405, 247; 549/13, 14, 21, 28, 60, 61, 63, 64, 65, 37, 38, 39, 59, 71, 72, 75, 77, 372, 376, 378, 414, 471, 474, 491, 4, 214; 556/33, 40, 85, 85; 564/87, 256; 558/412, 413, 414, 415; 560/107, 250, 251; 568/29, 30, 31, 36, 37, 42, 43

[56] References Cited

U.S. PATENT DOCUMENTS 4,249,937  2/1981  Iwataki et al. ............... 71/97
4,422,864  12/1983  Becker et al. ............... 71/88
4,596,877  7/1986  Becker et al. ............... 71/90
4,650,513  3/1987  Becker et al. ............... 71/88
4,758,265  7/1988  Becker et al. ............... 71/106
4,812,160  3/1989  Jahn et al. ............... 71/88
4,880,456  11/1989  Kolassa et al. ............... 71/88
4,909,835  3/1990  Tobler ............... 71/103
4,954,160  9/1990  Gilkerson et al. ............... 71/88
5,022,914  6/1991  Kast et al. ............... 71/88
5,074,903  12/1991  Jahn et al. ............... 71/90
5,076,831  12/1991  Saupe et al. ............... 71/90
5,190,573  3/1993  Misslitz et al. ............... 504/292
5,207,820  5/1993  Wriede et al. ............... 504/106
5,211,737  5/1993  Wriede et al. ............... 504/106
5,228,896  7/1993  Misslitz et al. ............... 504/288
5,250,505  10/1993  Kast et al. ............... 504/292
5,364,833  11/1994  Kast et al. ............... 504/289

FOREIGN PATENT DOCUMENTS 2011538  9/1990  Canada .
2041588  10/1991  Canada .
2041684  11/1991  Canada .
2046067  1/1992  Canada .
080301  6/1983  European Pat. Off. .
125094  11/1984  European Pat. Off. .
387582  9/1990  European Pat. Off. .

OTHER PUBLICATIONS

T. Gomyo et al., *Nippon Noyaku Gakkaishi*, vol. 12, No. 4, pp. 729 737, 1987.

Shoaf et al., *Weed. Sci.*, vol. 34, pp. 745–751, 1986.

Huber et al., *Brighton Crop Protection Conference*, 1988, Pests Dis. 1, pp. 335–341.

CA 108:203355r Residue . . . Crops. Gomyo et al., p. 562, 1988.

*Primary Examiner*—Joseph K. McKane
*Attorney, Agent, or Firm*—Keil & Weinkauf

[57] ABSTRACT

Cyclohexenone oxime ethers of the formula I

I $$\begin{array}{c} \text{structure with } R^3, R^4O, OH, NOR^2, R^1, O \end{array}$$

5 Claims, No Drawings

CYCLOHEXENONE OXIME ETHERS, THEIR PREPARATION AND THEIR USE

This application is a 371 of PCT/EP93/02158 filed Aug. 13, 1993.

The present invention relates to cyclohexenone oxime ethers of the formula I

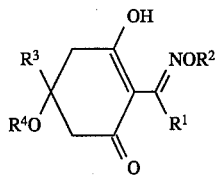

I in which the substituents have the following meanings:

$R^2$ is $C_1$-$C_6$-alkyl;

$R^2$ is $C_1$-$C_{10}$-alkyl, $C_1$-$C_{10}$-haloalkyl, $C_3$-$C_{10}$-alkenyl, $C_3$-$C_{10}$-haloalkenyl, $C_3$-$C_{10}$-alkynyl or $C_3$-$C_{10}$-haloalkynyl;

—$A^1$—O—N=CH—Ph or —$A^2$—W, where $A^1$ is $C_2$-$C_4$-alkylene which may carry from one to three $C_1$-$C_3$-alkyl groups;

Ph is phenyl which may be unsubstituted or may carry from one to three radicals selected from a group consisting of nitro, cyano, halogen, $C_1$-$C_4$-alkyl and $C_1$-$C_4$-haloalkyl;

$A^2$ is $C_1$-$C_6$-alkylene, $C_3$-$C_6$-alkenylene or $C_3$-$C_6$-alkynylene, where these radicals may in each case carry from one to three of the following groups: halogen and/or $C_1$-$C_3$-alkyl;

or is $C_2$-$C_5$-alkyleneoxy, $C_2$-$C_5$-alkenyleneoxy or $C_2$-$C_4$-alkyleneoxy-$C_1$-$C_3$-alkylene having a total of from three to five carbon atoms, where these radicals may in each case carry from one to three $C_1$-$C_3$-alkyl groups;

W is phenyl, pyridyl or thienyl, where the rings may in each case be unsubstituted or may carry from one to three of the following radicals: nitro, cyano, halogen, $C_1$-$C_4$-alkyl and/or $C_1$-$C_4$-haloalkyl;

$R^3$ is $C_1$-$C_6$-alkyl which carries one of the following groups: $C_1$-$C_4$-alkoxy or $C_1$-$C_4$-alkylthio;

$C_3$-$C_7$-cycloalkyl or $C_5$-$C_7$-cycloalkenyl, where these radicals may be unsubstituted or may carry from one to three of the following substituents: hydroxyl, halogen, $C_1$-$C_4$-alkyl, $C_1$-$C_4$-haloalkyl, $C_1$-$C_4$-alkoxy and/or $C_1$-$C_4$-alkylthio;

a 5-membered, saturated heterocyclic structure which, in addition to carbon ring members, may contain one or two oxygen and/or sulfur atoms, where this ring may be unsubstituted or may carry from one to three of the following substituents: $C_1$-$C_4$-alkyl, $C_1$-$C_4$-haloalkyl, $C_1$-$C_4$-alkoxy and/or $C_1$-$C_4$-alkylthio;

a 6-membered or 7-membered, saturated or mono- or di-unsaturated heterocyclic structure which, in addition to carbon ring members, may contain one or two oxygen and/or sulfur atoms, where this ring may be unsubstituted or may carry from one to three of the following substituents: hydroxyl, halogen, $C_1$-$C_4$-alkyl, $C_1$-$C_4$-haloalkyl, $C_1$-$C_4$-alkoxy and/or $C_1$-$C_4$-alkylthio;

a 5-membered heteroaromatic structure which, in addition to carbon ring members, contains one or two nitrogen atoms and one oxygen or one sulfur atom, where this ring may be unsubstituted or may carry from one to three of the following substituents: cyano, halogen, $C_1$-$C_4$-alkyl, $C_1$-$C_4$-haloalkyl, $C_1$-$C_4$-alkoxy, $C_1$-$C_4$-alkylthio, $C_2$-$C_6$-alkenyl, $C_2$-$C_6$-alkynyl and/or $C_1$-$C_4$-alkoxy-$C_1$-$C_4$-alkyl;

phenyl or pyridyl, where these rings may be unsubstituted or may carry from one to three of the following substituents: nitro, cyano, halogen, $C_1$-$C_4$-alkyl, $C_1$-$C_4$-haloalkyl, $C_1$-$C_4$-alkoxy, $C_1$-$C_4$-alkylthio, $C_3$-$C_6$-alkenyloxy, $C_3$-$C_6$-alkynyloxy and/or $NR^aR^b$, where $R^a$ is hydrogen, $C_1$-$C_4$-alkyl, $C_3$-$C_6$-alkenyl or $C_3$-$C_6$-alkynyl, and $R^b$ is one of the radicals $R^a$ or is $C_1$-$C_6$-alkylcarbonyl or benzoyl, where the phenyl ring in turn may carry from one to three of the following radicals: nitro, cyano, halogen, $C_1$-$C_4$-alkyl, $C_1$-$C_4$-haloalkyl, $C_1$-$C_4$-alkoxy and/or $C_1$-$C_4$-alkylthio;

$R^4$ is hydrogen;

$C_1$-$C_{10}$-alkyl, $C_1$-$C_{10}$-haloalkyl, $C_3$-$C_{10}$-alkenyl, $C_3$-$C_{10}$-haloalkenyl, $C_3$-$C_{10}$-alkynyl, $C_3$-$C_{10}$-haloalkynyl, $C_1$-$C_{10}$-alkylcarbonyl or $C_1$-$C_{10}$-haloalkylcarbonyl;

benzoyl, where the phenyl ring may be unsubstituted or may carry from one to three of the following radicals: nitro, cyano, halogen, $C_1$-$C_4$-alkyl, $C_1$-$C_4$-haloalkyl, $C_1$-$C_4$-alkoxy and/or $C_1$-$C_4$-alkylthio;

—$S(=O)_2$—$R^c$, —$P(=O)(OR^d)(OR^e)$ or —$SiR^fR^gR^h$, where $R^c$, $R^d$, $R^e$, $R^f$, $R^g$ and $R^h$ independently of one another are $C_1$-$C_{10}$-alkyl, $C_1$-$C_{10}$-haloalkyl or phenyl, where the phenyl ring in turn may carry from one to three of the following radicals: nitro, cyano, halogen, $C_1$-$C_4$-alkyl, $C_1$-$C_4$-haloalkyl, $C_1$-$C_4$-alkoxy and/or $C_1$-$C_4$-alkylthio, where $R^3$ is not S-oxo-2-(ethylthio)propyl, S,S-dioxo-2-(ethylthio)propyl, S-oxotetrahydrothiopyran-3-yl or S,S-dioxotetrahydrothiopyran-3-yl when $R^1$ is propyl, $R^2$ is ethyl and $R^4$ is hydrogen, and $R^3$ is not 2-(ethylthio)propyl, S-oxo-2-(ethylthio)-propyl or S,S-dioxo-2-(ethylthio)propyl when $R^1$ is ethyl, $R^2$ is 3-chloro-2-propenyl and $R^4$ is hydrogen, and $R^3$ is not S,S-dioxo-2-(ethylthio)propyl when $R^1$ is propyl, $R^2$ is ethyl and $R^4$ is methyl, and $R^3$ is not S,S-dioxo-2-(ethylthio)propyl when $R^1$ is ethyl, $R^2$ is 3-chloro-2-propenyl and $R^4$ is methyl, and the agriculturally useful salts of I and the esters of $C_1$-$C_{10}$-carboxylic acids or inorganic acids and the compounds I.

The present invention furthermore relates to processes and intermediates for the preparation of these cyclohexenone oxime ethers and to agents containing them and their use for controlling undesirable plant growth.

The literature [Nippon Noyaku Gakkaishi 12 (1987), 729; Weed Sci. 34 (1986), 745; Brighton Crop Prot. Conf.-Pests Dis. 1 (1988), 335] describes the compounds of the type of the cyclohexenone oxime ethers I listed in the table which follows as degradation products of known cyclohexenone herbicides:

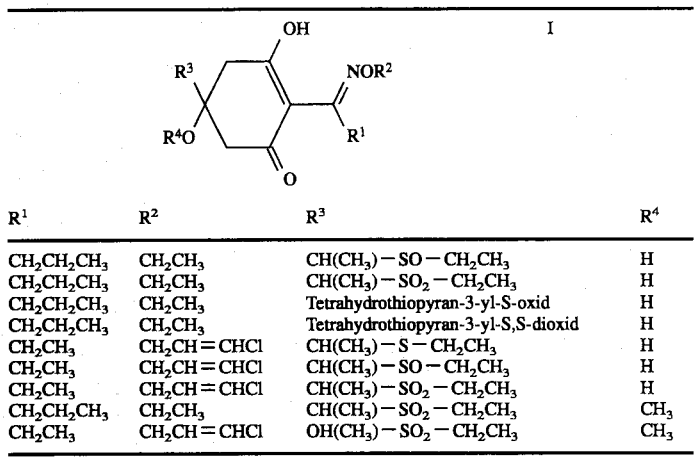

| $R^1$ | $R^2$ | $R^3$ | $R^4$ |
|---|---|---|---|
| $CH_2CH_2CH_3$ | $CH_2CH_3$ | $CH(CH_3)-SO-CH_2CH_3$ | H |
| $CH_2CH_2CH_3$ | $CH_2CH_3$ | $CH(CH_3)-SO_2-CH_2CH_3$ | H |
| $CH_2CH_2CH_3$ | $CH_2CH_3$ | Tetrahydrothiopyran-3-yl-S-oxid | H |
| $CH_2CH_2CH_3$ | $CH_2CH_3$ | Tetrahydrothiopyran-3-yl-S,S-dioxid | H |
| $CH_2CH_3$ | $CH_2CH=CHCl$ | $CH(CH_3)-S-CH_2CH_3$ | H |
| $CH_2CH_3$ | $CH_2CH=CHCl$ | $CH(CH_3)-SO-CH_2CH_3$ | H |
| $CH_2CH_3$ | $CH_2CH=CHCl$ | $CH(CH_3)-SO_2-CH_2CH_3$ | H |
| $CH_2CH_2CH_3$ | $CH_2CH_3$ | $CH(CH_3)-SO_2-CH_2CH_3$ | $CH_3$ |
| $CH_2CH_3$ | $CH_2CH=CHCl$ | $OH(CH_3)-SO_2-CH_2CH_3$ | $CH_3$ |

Cyclohexenone oxime ethers which carry only one substituent in the 5-position of the cyclohexenone ring are disclosed as herbicides in many publications (EP-A 368,227; EP-A 080,301; EP-A 125,094; EP-A 238,021; EP-A 243,313; EP-A 456,068; EP-A 456,069; EP-A 456,089; EP-A 456,112; EP-A 456,118; EP-A 066,195; U.S. Pat. No. 4,249,937).

Furthermore, cyclohexenone oxime ethers which carry two substituents in the 5-position of the cyclohexenone ring, one of which is hydroxyl, are described in general form by the following publications: EP-A 385,084; EP-A 380,985; EP-A 387,568; EP-A 387,582; EP-A 459,140; EP-A 430,004; EP-A 464,542. Examples of compounds of this type and of their activity are, however, not described in the publications cited.

It was an object of the present invention to provide novel herbicidal active ingredients having improved properties.

Accordingly, the cyclohexenone oxime ethers I defined at the outset were found. Furthermore, processes and intermediates for their preparation and their use in herbicides for controlling undesirable plant growth have been found.

The novel cyclohexenone oxime ethers I are obtainable by various methods described in the literature cited at the outset.

The compounds of the formula Ia (cyclohexenone oxime ethers of the formula I in which $R^4$ is hydrogen) are particularly advantageously obtained by a method in which a triketone of the formula II is cyclized in a conventional manner, in an inert organic solvent in the presence of a base, with an acyl halide of the formula III to give a cyclohexenone ketone of the formula IV, and IV is then reacted in a conventional manner, in an inert organic solvent, with a hydroxylamine of the formula V or with a corresponding hydroxylammonium salt.

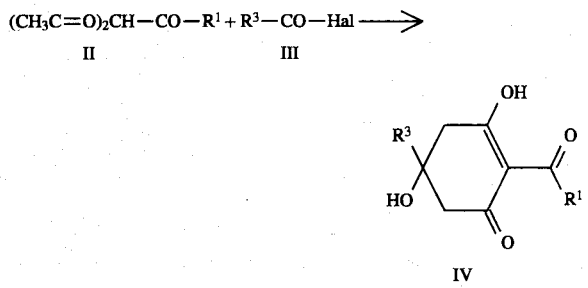

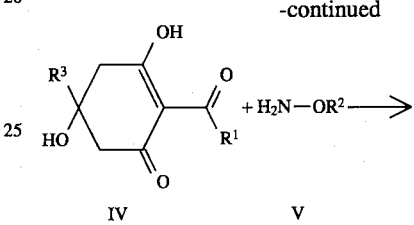

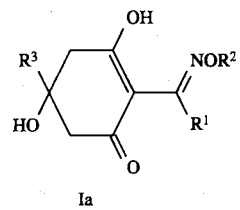

In the formula III, Hal is halogen, such as fluorine, chlorine, bromine and iodine, preferably chlorine and bromine.

Specifically, the reactions are carried out as follows:

The cyclohexenone ketone of the formula IV is prepared in a conventional manner (Angew. Chem. 101 (1989), 484; Chem. Ber. 124 (1991), 1845) at from (−105)° C. to 25° C., preferably from (−78)° C. to 0° C., in an inert organic solvent in the presence of a base.

Suitable solvents are aliphatic and aromatic hydrocarbons, such as pentans, hexane, cyclohexane, petroleum ether and toluene, and ethers, such as diethyl ether, ethylene glycol dimethyl ether, diethylene glycol dimethyl ether, dioxane and tetrahydrofuran; tetrahydrofuran, is particularly preferred. Mixtures of the stated solvents may also be used, however.

Suitable bases are in general hydrides, amides, alcoholates and alkyls of alkali metal and alkaline earth metal ions. Examples of suitable bases are hydrides, such as lithium hydride, sodium hydride, potassium hydride and calcium hydride, alkali metal amides, such as lithium amide, sodium amide and potassium amide, dialkylamides of lithium or sodium, such as N,N-dimethylamide, N,N-diethylamide, N,N-diisopropylamide and 2,2,6,6-tetramethylpiperidide, as well as alkali metal alkyls, such as methyllithium and butyllithium, phenyllithium as well as alkali metal and alkaline earth metal alcoholates, such as sodium methylate, sodium ethylate, potassium ethylate, potassium tert-butylate and magnesium ethylate, preferably lithium N,N-diisopropylamide and lithium N,N-(bistrimethylsilyl)-amide.

The bases are used in general in equimolar amounts. Accordingly, 3 mol equivalents of the base are usually used per mol of triketone II (corresponding to 1 mol equivalent of base per keto function). It may be advantageous to use the base in an excess, for example of up to about 30 mol %.

According to previous knowledge this reaction advantageously takes place in the presence of a solubilizer or of an auxiliary reagent N,N,N',N'-Tetramethylethylenediamine, hexamethylphosphorotriamide, N,N'-dimethylpropyleneurea and N,N'-dimethylethyleneurea have proven particularly suitable in this respect.

The auxiliary reagent is used in general in about equimolar amounts based on the amount of base employed.

The starting materials are generally reacted with one another in equimolaramounts. It may be advantageous for the yield to use the acyl halide III in an excess, based on the triketone II.

In the reaction, the triketone II is usually first enolized with the base, and the acyl halide is then added.

The reaction mixtures are worked up in a conventional manner, for example by mixing with water, separation of the phases and, if required, chromatographic purification of the crude products. Some of the intermediates and end products are obtained in the form of colorless or slightly brownish, viscous oils which are freed from volatile components or purified under reduced pressure and at moderately elevated temperatures. If the intermediates and end products are obtained as solids, purification may also be effected by recrystallization or digestion.

The starting materials II and III required for the preparation of the compounds IV are known in the literature (JP-A 49/034,650; U.S. Pat. No. 3,947,488; Organikum, 17th Edition, page 423 et seq., VEB Deutscher Verlag der Wissenschaften, Berlin 1988) or can be prepared according to the literature cited.

The reaction of the cyclohexenone ketone of the formula IV with a hydroxylamine of the formula V or with a corresponding ammonium salt is carried out in a conventional manner (according to the literature cited at the outset) at from 0° C. to the boiling point of the solvent used, preferably from 20° to 80° C. in an inert organic solvent. If the hydroxylamine is used in the form of its salt, the reaction additionally requires the presence of a base.

Suitable solvents are aliphatic hydrocarbons, such as pentane, hexane, cyclohexane and petroleum ether, aromatic hydrocarbons, such as toluene and o-, m- and p-xylene, halohydrocarbons, such as methylene chloride, chloroform, 1,2-dichloroethane and chlorobenzene, alcohols, such as methanol, ethanol, n-propanol and isopropanol, ethers, such as diethyl ether, diisopropyl ether, tert-butyl methyl ether, ethylene glycol dimethyl ether, diethylene glycol dimethyl ether, dioxane and tetrahydrofuran, organic esters, such as ethyl acetate, and dimethyl sulfoxide; toluene and methanol are particularly preferred. Mixtures of the stated solvents may also be used, however.

In the reaction of the ammonium salts, bases, such as carbonates, bicarbonates, acetates, alcoholates, hydroxides or oxides of alkali metal and alkaline earth metal ions, are generally used. Examples of suitable bases are alkali metal and alkaline earth metal carbonates, such as lithium carbonate and calcium carbonate, alkali metal bicarbonates, such as sodium bicarbonate, alkali metal acetates, such as sodium acetate, alkali metal and alkaline earth metal alcoholates, such as sodium methylate, sodium ethylate, potassium ethylate, potassium tert-butylate and dimethoxy-magnesium, alkali metal and alkaline earth metal hydroxides, such as lithium hydroxide, sodium hydroxide, potassium hydroxide and calcium hydroxide, and alkali metal and alkaline earth metal oxides, such as lithium oxide, sodium oxide, calcium oxide and magnesium oxide.

The reaction of ammonium salts of the compounds V with IV is particularly preferably carried out in methanol as the solvent and, if required, with sodium bicarbonate as the base.

The bases are used in general in amounts of from 0.5 to 2 mol equivalents, based on the amount of ammonium salt.

If, instead of the ammonium salts, the free bases V are used for the reaction, the hydroxylamine is usually employed in the form of its aqueous solution.

Accordingly, the reaction can be carried out in a single-phase or two-phase solvent system, depending on the organic solvent.

For example, alcohols, such as methanol, ethanol, isopropanol and cyclohexanol, aliphatic and aromatic hydrocarbons and halohydrocarbons, such as hexane, cyclohexane, toluene, methylene chloride and 1,2-dichloroethane, nitriles, such as acetonitrile, and ethers, such as dioxane and tetrahydrofuran, are suitable solvents for this variant.

The starting materials IV and V are generally reacted with one another in equimolar amounts. It may be advantageous for the yield to use one of the starting materials in an excess of up to about 10 mol %.

The reaction mixtures are worked up in a conventional manner, for example by mixing with water, separation of the phases and, if required, chromatographic purification of the crude products. Some of the intermediates and end products are obtained in the form of colorless or slightly brownish, viscous oils which are freed from volatile components or purified under reduced pressure and at moderately elevated temperatures. If the intermediates and end products are obtained as solids, purification may also be effected by recrystallization or digestion.

The hydroxylamines V required for the preparation of the compounds Ia, and the ammonium salts of said hydroxylamines, are known from the literature cited at the outset or can be prepared by the methods described there.

Hydroxylamines of the formula Va

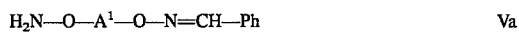
$$H_2N-O-A^1-O-N=CH-Ph \qquad Va$$

where $A^1$ and Ph have the abovementioned meanings, are novel.

They are obtained, for example, by reacting a bisaminooxyalkane of the formula VII in a conventional manner (Angew. Makromol. Chem. 184 (1985), 125; Bioorg. Khim. 11 (1985), 1574; J. Org. Chem. 54 (1989), 2351; Houben-Weyl, Methoden der organischen Chemie, Vol. E 14b, page 369) in an inert organic solvent with an aldehyde of the formula VIII.

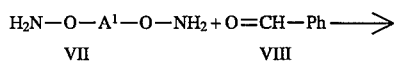
$$H_2N-O-A^1-O-NH_2 + O=CH-Ph \longrightarrow$$
$$\qquad VII \qquad\qquad VIII$$

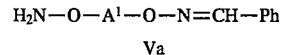
$$H_2N-O-A^1-O-N=CH-Ph$$
$$Va$$

This reaction is usually carried out at from 0° to 110° C. preferably from 20° to 50° C.

Suitable solvents are aliphatic hydrocarbons, such as pentane, hexane, cyclohexane and petroleum ether, aromatic hydrocarbons, such as toluene and o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, alcohols, such as methanol, ethanol, n-propanol, isopropanol, n-butanol and tert-butanol, and dimethyl sulfoxide and dimethylformamide; toluene and methanol are particularly preferred. Mixtures of the stated solvents may also be used, however.

The starting materials are generally reacted with one another in equimolar amounts. It may be advantageous for the yield to use an excess of bisaminooxyalkane of the formula VII, based on the aldehyde of the formula VIII, since bis(benzylideneiminoxy)alkanes of the formula IX may form as byproducts.

Ph—HC=N—O—A$^1$—O—N=CH—Ph    IX

Starting from the compounds of the formula Ia, the compounds of the formula Ib are obtained by reacting a compound Ia in a conventional manner (Organikum, 17th Edition, page 198 et seq., page 214 et seq., page 407 et seq., VEB Deutscher Verlag der Wissenschaften, Berlin 1988) in an inert organic solvent with a compound of the formula VI.

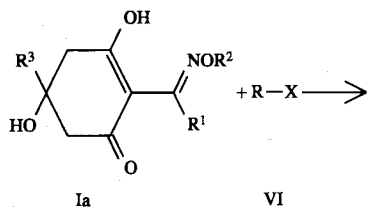

Ia    VI

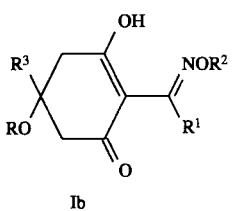

Ib

In the formulae VI and Ib, R is one of the radicals $R^4$ according to the definition given at the outset, with the exception of hydrogen.

In the formula VI, X is halogen, such as fluorine, chlorine, bromine and iodine, preferably chlorine, bromine and iodine.

Depending on the meaning of R in the formula VI, the groups X and the reaction conditions differ:

A: If R is alkyl, alkenyl or alkynyl, X is in particular chlorine, bromine or iodine.

In this case, the reaction of Ia with VI is carried out by the etherification methods known generally from the literature (reference: eg. Organikum, 17th Edition, page 198 et seq., VEB Deutscher Verlag der Wissenschaften, Berlin 1988).

This reaction is usually carried out at from 0° to 150° C., preferably from 50° to 100° C.

Suitable solvents are aliphatic hydrocarbons, such as pentane, hexane, cyclohexane and petroleum ether, aromatic hydrocarbons, such as toluene and o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, and dimethyl sulfoxide and dimethylformamide; dimethyl sulfoxide, dimethylformamide and acetonitrile are particularly preferred.

Mixtures of the stated solvents may also be used.

B: If R is alkylcarbonyl, benzoyl, —S(=O)$_2$—R$^c$, —P(=O)(OR$^d$)(OR$^e$) or —SiR$^f$R$^g$R$^h$, X is in particular chlorine.

In this case, the reaction of Ia with VI is carried out by the esterification methods generally known from the literature (reference: eg. Organikum, 17th Edition, page 407 et seq., VEB Deutscher Verlag der Wissenschaften, Berlin 1988).

This reaction is usually carried out at from (–10)° C. to 100° C. preferably from 0° to 50° C.

Suitable solvents are aliphatic hydrocarbons, such as pentane, hexane, cyclohexane and petroleum ether, aromatic hydrocarbons, such as toluene and o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, particularly preferably halohydrocarbons. Mixtures of the stated solvents may also be used.

The cyclohexenone oxime ethers of the formula I may be obtained as isomer mixtures in the preparation, both E/Z isomer mixtures and enantiomer or diastereomer mixtures being possible. These mixtures can, if required, be separated by the conventional methods, for example by chromatography or fractional crystallization.

The general formula I is typical of all possible tautomeric forms in which the cyclohexenone oxime ether I may occur.

In view of the use of the compounds I as active ingredients, the substituents defined at the outset are the following radicals. The definitions of the substituents in the intermediates IV and Va are also to be similarly understood.

$R^1$ is $C_1$-$C_6$-alkyl, such as methyl, ethyl n-propyl, 1-methylethyl, n-butyl, 1-methylpropyl 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, in particular ethyl and n-propyl;

$R^2$ is $C_1$-$C_{10}$-alkyl, in particular $C_1$-$C_6$-alkyl as stated above, in particular ethyl;

partially or completely halogenated $C_1$-$C_{10}$-alkyl, preferably $C_1$-$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, in particular 2-fluoroethyl;

$C_3$-$C_{10}$-alkenyl, in particular $C_3$-$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1,-dimethyl-2-propenyl, 1,2-dimethyl- 2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl- 3-butenyl, 1,2-dimethyl-2-butenyl, 1,2-dimethyl-3 -butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl- 2-butenyl, 1-ethyl-3-butenyl, 2-ethyl-2-butenyl, 2-ethyl- 3-butenyl, 1,1,2-trimethyl-2-propenyl, 1-ethyl-1-methyl- 2-propenyl and 1-ethyl-2-methyl-2-propenyl, in particular 2-propenyl and (E)-2-butenyl;

partially or completely halogenated $C_3$-$C_{10}$-alkenyl, such as $C_3$-$C_{10}$-alkenyl as stated above in general, which is partially or completely substituted by halogen, in particular fluorine and/or chlorine, in particular (E)-3-chloro- 2-propenyl;

$C_3$-$C_{10}$-alkynyl, in particular $C_3$-$C_6$-alkynyl, such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl- 2-butynyl, 1-ethyl-3-butynyl, 2-ethyl-3-butynyl and 1-ethyl-1-methyl-2-propynyl, in particular 2-propynyl;

or partially or completely halogenated $C_3$-$C_{10}$-alkynyl, in particular $C_3$-$C_{10}$-alkynyl substituted by fluorine and/or chlorine as stated above in general and in particular;

—$A^1$—O—N=CH—Ph or —$A^2$—W; in which $A^1$ is $C_2$-$C_4$-alkylene, such as —$CH_2CH_2$—, —$CH_2CH_2CH_2$— and —$CH_2CH_2CH_2CH_2$—, which may carry from one to three $C_1$-$C_3$-alkyl groups, such as methyl, ethyl, propyl and 1-methylethyl, in particular methyl;

Ph is phenyl which may carry from one to three of the following groups:

nitro, cyano, halogen, such as fluorine, chlorine, bromine and iodine, in particular fluorine and chlorine, $C_1$-$C_4$-alkyl, such as methyl, ethyl, n-propyl, 1-methylethyl, n-butyl, 1-methylpropyl, 2-methylpropyl and 1,1-dimethylethyl, in particular methyl, and/or $C_1$-$C_4$-haloalkyl as stated above, in particular trifluoromethyl;

$A^2$ is $C_1$-$C_6$-alkylene, such as —$CH_2$—, —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$—, or $C_3$-$C_6$-alkenylene, such as —$CH_2CH=CH$—, —$CH_2CH=CHCH_2$—, —$CH_2CH_2CH=CH$—, —$CH_2CH=CHCH_2$—, —$CH_2CH_2CH=CHCH_2$—, —$CH_2CH_2CH_2CH=CH$—, —$CH_2CH=CHCH_2CH_2$—, —$CH_2CH_2CH=CHCH_2$—, —$CH_2CH_2CH_2CH=CHCH_2$— or —$CH_2CH_2CH_2CH_2CH=CH$—, or $C_3$-$C_6$-alkynylene, such as —$CH_2C\equiv C$—, —$CH_2C\equiv CCH_2$—, —$CH_2CH_2C\equiv C$—, —$CH_2C\equiv CCH_2CH_2$—, —$CH_2CH_2C\equiv CCH_2$—, —$CH_2CH_2CH_2C\equiv C$—, —$CH_2C\equiv CCH_2CH_2$—, —$CH_2CH_2C\equiv CCH_2$—, —$CH_2CH_2CH_2C\equiv CCH_2$— and —$CH_2CH_2CH_2CH_2C\equiv C$—, where these radicals may carry from one to three of the following groups:

halogen as stated above, in particular fluorine and chlorine, and/or $C_1$-$C_3$-alkyl, such as methyl, ethyl, propyl and 1-methylethyl, in particular methyl;

or $C_2$-$C_5$alkyleneoxy, $C_2$-$C_5$-alkenyleneoxy, such as —$CH_2CH_2O$—, —$CH_2CH_2CH_2O$—, —$CH_2CH_2CH_2CH_2O$— and —$CH_2CH_2CH_2CH_2CH_2O$—, or $C_2$-$C_4$-alkyleneoxy-$C_1$-$C_3$-alkylene having a total of from three to five carbon atoms, such as —$CH_2CH_2OCH_2$—, —$CH_2CH_2OCH_2CH_2$—, —$CH_2CH_2CH_2OCH_2CH_2$— and —$CH_2CH_2CH_2CH_2OCH_2$—, where these radicals may carry from one to three $C_1$-$C_3$-alkyl groups as stated above, preferably methyl and ethyl, in particular methyl;

W is phenyl, pyridyl or thienyl, where these radicals may carry from one to three of the following groups:

nitro, cyano halogen as stated above, in particular fluorine or chlorine, $C_1$-$C_4$-alkyl as stated above, in particular methyl, and/or $C_1$-$C_4$-haloalkyl as stated above, in particular trifluoromethyl;

$R^2$ is particularly preferably $C_1$-$C_{10}$-alkyl, $C_1$-$C_{10}$-haloalkyl, $C_3$-$C_{10}$-alkenyl, $C_3$-$C_{10}$ haloalkenyl or —$A^2$—W;

$R^3$ is $C_1$-$C_6$-alkyl as stated above, in particular propyl, which carries one of the following groups:

$C_1$-$C_4$-alkoxy, such as methoxy, ethoxy, propoxy, 1-methylethoxy, butoxy, 1-methylpropoxy, 2-methylpropoxy and 1,1-dimethylethoxy, in particular methoxy, ethoxy, or $C_1$-$C_4$-alkylthio, such as methylthio, ethylthio, propylthio, 1-methylethylthio, butylthio, 1-methylpropylthio, 2-methylpropylthio and 1,1-dimethylethylthio, in particular methylthio, ethylthio;

particularly preferred is $C_1$-$C_4$-alkylthio-$C_1$-$C_6$-alkyl;

$C_3$-$C_7$-cycloalkyl, such as cyclopropyl, cyclobutyl, cyclopentyl, cyclohexyl, cycloheptyl and cyclooctyl, in particular cyclopropyl, cyclohexyl, or $C_5$-$C_7$-cycloalkenyl, such as cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl and cyclohept-4-enyl, in particular cyclohex-3-enyl, where these radicals may carry from one to three substituents selected from a group consisting of:

hydroxyl, halogen as stated above, in particular fluorine or chlorine, $C_1$-$C_4$-alkyl as stated above, in particular methyl, $C_1$-$C_4$-haloalkyl as stated above, in particular trifluoromethyl, $C_1$-$C_4$-alkoxy as stated above, in particular methoxy, and/or $C_1$-$C_4$-alkylthio as stated above, in particular methylthio;

particularly preferred is $C_3$-$C_7$-cycloalkyl which may carry a $C_1$-$C_4$-alkylthio group;

a 5-membered, saturated heterocyclic structure which, in addition to carbon ring members, may contain one or two oxygen and/or sulfur atoms, such as 2-tetrahydrofuranyl, 3-tetrahydrofuranyl, 2-tetrahydrothienyl, 3-tetrahydrothienyl, 1,3-dioxolan-2-yl, 1,3-dioxolan-4-yl, 1,3-dithiolan-2-yl, 1,3-dithiolan-4-yl, 1,3-thioxolan-2-yl, 1,3-dioxolan-4-yl and 1,3-dioxolan-5-yl, where this ring may carry from one to three substituents selected from a group consisting of:

$C_1$-$C_4$-alkyl as stated above, in particular methyl, $C_1$-$C_4$-haloalkyl as stated above, in particular trifluoromethyl, $C_1$-$C_4$-alkoxy as stated above, in particular methoxy, and $C_1$-$C_4$-alkylthio as stated above, in particular methylthio;

a 6-membered or 7-membered, saturated or mono- or diunsaturated heterocyclic structure which, in addition to carbon ring members, may contain one or two oxygen and/or sulfur atoms, such as tetrahydropyan-2-yl, tetrahydropyran-3-yl, tetrahydropyran-4-yl, tetrahydrothiopyran- 2-yl, tetrahydrothiopyran-3-yl, tetrahydrothiopyran- 4-yl, 1,3-dioxepan-5-yl, 1,4-dioxepan-5-yl, 3,4-dihydro-2H-pyran-2-yl, 5,6-dihydro-2H-pyran-2-yl, 2,3-dihydro-4H-pyran-2-yl, 5,6-dihydro-4H-pyran-2-yl, 3,4-dihydro-2H-pyran-3-yl, 5,6-dihydro-2H-pyran-3-yl, 2,3-dihydro-4H-pyran-3-yl, 5,6-dihydro-4H-pyran-3-yl, 3,4-dihydro-2H-pyran-4-yl, 5,6-dihydro-2H-pyran-4-yl, 2,3-dihydro-4H-pyran-4-yl, 3,4-dihydro-2H-thiopyran-2-yl, 5,6-dihydro-2H-thiopyran-2-yl, 2,3-dihydro-4H-thiopyran- 2-yl, 5,6-dihydro-4H-thiopyran-2-yl, 3,4-dihydro- 2H-thiopyran-3-yl, 5,6-dihydro-2H-thiopyran-3-yl, 2,3-dihydro-4H-thiopyran-3-yl, 5,6-dihydro-4H-thiopyran- 3-yl, 3,4-dihydro-2H-thiopyran-4-yl, 5,6-dihydro-2H-thiopyran- 4-yl and 2,3-dihydro-4H-thiopyran-4-yl, where this ring may carry from one to three substituents selected from a group consisting of:

hydroxyl, halogen as stated above, in particular fluorine or chlorine, $C_1$-$C_4$-alkyl as stated above, in particular methyl, $C_1$-$C_4$-haloalkyl as stated above, in particular trifluoromethyl, $C_1$-$C_4$-alkoxy as stated above, in particular methoxy, and $C_1$-$C_4$-alkylthio as stated above, in particular methylthio;

particularly preferred is a 6-membered saturated heterocycle which may contain, in addition to carbon ring members, one or two oxygen atoms and/or sulfur atoms;

a 5-membered heteroaromatic structure which, in addition to carbon ring members, contains one or two nitrogen atoms and one oxygen or one sulfur atom, such as 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol- 5-yl, 1,2,4-triazol-3-yl, 1,3,4-oxadiazol-2-yl, 1,3,4-thiadiazol-2-yl and 1,3,4-triazol-2-yl, in particular 5-isoxazolyl, where this ring may carry from one to three substituents selected from a group consisting of:

cyano, halogen as stated above, in particular fluorine or chlorine, $C_1$-$C_4$-alkyl as stated above, preferably 1-methylethyl, methyl, in particular 1-methylethyl, $C_1$-$C_4$-haloalkyl as stated above, in particular trifluoromethyl, $C_1$-$C_4$-alkoxy as stated above, preferably 1-methylethoxy, methoxy, in particular methoxy, $C_1$-$C_4$-alkylthio as stated above, in particular methylthio, $C_2$-$C_6$-alkenyl, such as ethenyl, 1-propenyl, 2-propenyl, 1-methylethenyl, 1-butenyl, 2-butenyl, 3-butenyl, 1-methyl- 1-propenyl, 2-methyl- 1-propenyl, 1-methyl-2-propenyl, 2-methyl- 2-propenyl, 1-pentenyl, 2-pentenyl, 3-pentenyl, 4-pentenyl, 1-methyl- 1-butenyl, 2-methyl- 1-butenyl, 3-methyl- 1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl- 1-propenyl, 1-ethyl-2-propenyl, 1-hexenyl, 2-hexenyl, 3-hexenyl, 4-hexenyl, 5-hexenyl, 1-methyl-1-pentenyl 2-methyl-1-pentenyl, 3-methyl-1-pentenyl, 4-methyl- 1-pentenyl, 1-methyl-2-pentenyl, 2-methyl-2-pentenyl, 3-methyl-2-pentenyl, 4-methyl-2-pentenyl, 1-methyl- 3 -pentenyl, 2-methyl-3-pentenyl, 3-methyl-3-pentenyl, 4-methyl-3-pentenyl, 1-methyl-4-pentenyl, 2-methyl- 4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl- 1-butenyl, 1,3-dimethyl- 2-butenyl, 1,3-dimethyl-3-butenyl, 2,2-dimethyl- 3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, preferably ethenyl, 2-propenyl or 2-butenyl, in particular 2-propenyl, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl- 1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl- 4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl- 2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl, preferably ethynyl, 2-propynyl, 2-butynyl, in particular 2-propynyl, and $C_1$-$C_4$-alkoxy-$C_1$-$C_4$-alkyl, such as methoxy-, ethoxy-, propoxy-, 1-methylethoxy-, butoxy-, 1-methylpropoxy-, 2-methylpropoxy- and 1,1-dimethylethoxy-substituted, in particular methoxy-substituted, $C_1$-$C_4$-alkyl as stated above, in particular ethyl;

amongst substituents of the 5-membered heteroaromatic group $C_1$-$C_4$-alkyl is particularly preferred;

phenyl or pyridyl, where these rings may carry from one to three substituents selected from a group consisting of:

nitro, cyano, halogen as stated above, in particular fluorine or chlorine, $C_1$-$C_4$-alkyl as stated above, in particular methyl, $C_1$-$C_4$-haloalkyl as stated above, in particular trifluoromethyl, $C_1$-$C_4$-alkoxy as stated above, in particular methoxy, $C_1$-$C_4$-alkylthio as stated above, in particular methylthio, $C_3$-$C_6$-alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl- 2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl- 2-propenyloxy, 1-ethyl-2propenyloxy, 2-hexenyloxy, 3-hexenyloxy, 4-hexenyloxy, 5-hexenyloxy, 1-methyl- 2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl- 4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 3,3-dimethyl-2-butenyloxy, 1-ethyl-2-butenyloxy, 1-ethyl-3-butenyloxy, 2-ethyl- 2-butenyloxy, 2-ethyl-3-butenyloxy, 1,1,2-trimethyl-2-propenyloxy, 1-ethyl-1-methyl-2-propenyloxy and 1-ethyl- 2-methyl-2-propenyloxy, in particular 2-propenyloxy, $C_3$-$C_6$-alkynyloxy, such as 2-propynyloxy, 2-butynyloxy, 3-butynyloxy, 1-methyl-2-propynyloxy, 2-pentynyloxy, 3-pentynyloxy, 4-pentynyloxy, 1-methyl-2-butynyloxy, 1-methyl- 3-butynyloxy, 2-methyl-3-butynyloxy, 1,1-dimethyl- 2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-2-pentynyloxy, 1,1-dimethyl- 2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy and 1-ethyl-1-methyl-2-propynyloxy, in partiuclar 2-propynyloxy, and a substituent $NR^aR^b$;

$R^a$ is hydrogen, is $C_1$-$C_4$-alkyl as stated above, in particular methyl, is $C_3$-$C_6$-alkenyl as stated above, in particular 2-propenyl, 2-butenyl, or is $C_3$-$C_6$-alkynyl as stated above, in particular 2-propynyl, 2-butynyl $R^b$ is hydrogen, is $C_1$-$C_4$-alkyl as stated above, in particular methyl, is $C_3$-$C_6$-alkenyl as stated above, in particular 2-propenyl, 2-butenyl, or is $C_3$-$C_6$-alkynyl as stated above, in particular 2-propynyl 2-butynyl is $C_1$-$C_6$-alkylcarbonyl, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl,pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2- dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl, in particular methylcarbonyl, ethylcarbonyl, or is benzoyl, where the phenyl ring may in turn carry from one to three of the following radicals:

nitro, cyano, halogen as stated above, in particular fluorine or chlorine, $C_1$-$C_4$-alkyl as stated above, in particular methyl, $C_1$-$C_4$-haloalkyl as stated above, in particular trifluoromethyl, $C_1$-$C_4$-alkoxy as stated above, in particular methoxy, and/or $C_1$-$C_4$-alkylthio as stated above, in particular methylthio; particularly preferred is phenyl which may carry from one to three nitro, halogen and/or $C_1$-$C_4$-alkyl substituents;

$R^4$ is hydrogen;

$C_1$-$C_{10}$-alkyl, in particular $C_1$-$C_6$-alkyl as stated above, in particular methyl, $C_1$-$C_{10}$-haloalkyl as stated above in general and in particular, in particular trifluoromethyl, $C_3$-$C_{10}$-alkenyl, in particular $C_3$-$C_6$-alkenyl as stated above, $C_3$-$C_{10}$-haloalkenyl as stated above in general and in particular, in particular 2-propenyl, $C_3$-$C_{10}$-alkynyl as stated above, in particular 2-propynyl, $C_3$-$C_{10}$-haloalkynyl as stated above in general and in particular, $C_1$-$C_{10}$-alkylcarbonyl, in particular $C_1$-$C_6$-alkylcarbonyl as stated above, in particular methylcarbonyl, $C_1$-$C_{10}$-haloalkylcarbonyl as stated above in general and in particular;

benzoyl, where the phenyl ring may carry from one to three of the following groups:

nitro, cyano, halogen as stated above, in particular fluorine and chlorine, $C_1$-$C_4$-alkyl as stated above, in particular methyl, $C_1$-$C_4$-haloalkyl as stated above, in particular trifluoromethyl, $C_1$-$C_4$-alkoxy as stated above, in particular methoxy, and/or $C_1$-$C_4$-alkylthio as stated above, in particular methylthio; or —S(=O)$_2$—$R^c$, —P(=O)(OR$^d$)(OR$^e$) or —SiR$^f$R$^g$R$^h$, and R$^c$, R$^d$, R$^e$, R$^f$, R$^g$ and R$^h$ independently of one another are each $C_1$-$C_{10}$-alkyl, in particular $C_1$-$C_6$-alkyl as stated above, preferably methyl, ethyl, 1,1-dimethylethyl, in particular methyl, $C_1$-$C_{10}$-haloalkyl as stated above in general and in particular, or phenyl, where the phenyl ring may carry from one to three of the following radicals:

nitro, cyano, halogen as stated above, in particular fluorine or chlorine, $C_1$-$C_4$-alkyl as stated above, in particular methyl, $C_1$-$C_4$-haloalkyl as stated above, in particular trifluoromethyl, $C_1$-$C_4$-alkoxy as stated above, in particular methoxy, and/or $C_1$-$C_4$-alkylthio as stated above, in particular methylthio.

$R^4$ is particularly preferably hydrogen.

The present invention does not relate to cyclohexenone oxime ethers of the formula I in which $R^3$ is S-oxo-2-(ethylthio)propyl, S,S-dioxo-2-(ethylthio)propyl, S-oxotetrahydrothiopyran-3-yl or S,S-dioxotetrahydrothiopyran-3-yl when $R^1$ is propyl, $R^2$ is ethyl and $R^4$ is hydrogen, or in which $R^3$ is 2-(ethylthio)propyl, S-oxo-2-(ethylthio)propyl or S,S-dioxo-2-(ethylthio)propyl when $R^1$ is ethyl, $R^2$ is 3-chloro- 2-propenyl and $R^4$ is hydrogen, $R^3$ is S,S-dioxo-2-(ethylthio)propyl when $R^1$ is propyl, $R^2$ is ethyl and $R^4$ is methyl, or in which $R^3$ is S,S-dioxo-2-(ethylthio)propyl when $R^1$ is ethyl, $R^2$ is 3-chloro-2-propenyl and $R^4$ is methyl.

However, the present invention also relates to the agriculturally useful salts of I as well as the esters of $C_1$-$C_{10}$-carboxylic acids or inorganic acids and the compounds I. Here, the type of salt or of ester is usually not important. In general, the salts of those bases and those esters which do not adversely affect the herbicidal action of the compounds I are suitable.

Agriculturally useful salts of the compounds I are, for example, alkali metal salts, in particular sodium and potassium salts, alkaline earth metal salts, in particular calcium, magnesium and barium salts, manganese, copper, zinc or iron salts and ammonium salts, such as tetraalkyl- and benzyltrialkylammonium salts, phosphonium and sulfonium salts, such as trialkylsulfonium salts, or sulfoxonium salts.

Agriculturally useful esters are, for example, the esters of cyclohexenone oxime ethers I with $C_1$-$C_{10}$-fatty acids, in particular $C_1$-$C_6$-alkanecarboxylic acids, such as methanecarboxylic acid (acetic acid), ethanecarboxylic acid (propionic acid), propanecarboxylic acid (butyric acid), 1-methylethanecarboxylic acid (isobutyric acid), butanecarboxylic acid, 1-methylpropanecarboxylic acid, 2-methylpropanecarboxylic acid, 1,1-dimethylethanecarboxylic acid, pentanecarboxylic acid, 1-methylbutanecarboxylic acid, 2-methylbutanecarboxylic acid, 3-methylbutanecarboxylic acid, 1,1-dimethylpropanecarboxylic acid, 1,2-dimethylpropanecarboxylic acid, 2,2-dimethylpropanecarboxylic acid and 1-ethylpropanecarboxylic acid, benzoic acid and corresponding derivatives substituted in the phenyl nucleus, hexanecarboxylic acid, 1-methylpentanecarboxylic acid, 2-methylpentanecarboxylic acid, 3-methylpentanecarboxylic acid, 4-methylpentanecarboxylic acid, 1,1-dimethylbutanecarboxylic acid, 1,2-dimethylbutanecarboxylic acid, 1,3-dimethylbutanecarboxylic acid, 2,2-dimethylbutanecarboxylic acid, 2,3-dimethylbutanecarboxylic acid, 3,3-dimethylbutanecarboxylic acid, 1-ethylbutanecarboxylic acid, 2-ethylbutanecarboxylic acid, 1,1,2-trimethylpropanecarboxylic acid, 1,2,2-trimethylpropanecarboxylic acid, 1-ethyl-1-methylpropanecarboxylic acid and 1-ethyl-2-methylpropanecarboxylic acid;

$C_1$-$C_{20}$-sulfonic acids, in particular $C_1$-$C_6$-alkanesulfonic acids, such as methanesulfonic acid, ethanesulfonic acid, propanesulfonic acid, 1-methylethanesulfonic acid, butanesulfonic acid, 1-methylpropanesulfonic acid, 2-methylpropanesulfonic acid, 1,1-dimethylethanesulfonic acid, pentanesulfonic acid, 1-methylbutanesulfonic acid, 2-methylbutanesulfonic acid, 3-methylbutanesulfonic acid, 1,1-dimethylpropanesulfonic acid, 1,2-dimethylpropanesulfonic acid, 2,2-dimethylpropanesulfonic acid and 1-ethylpropanesulfonic acid, benzenesulfonic acid and corresponding derivatives substituted in the phenyl nucleus, hexanesulfonic acid, 1-methylpentanesulfonic acid, 2-methylpentanesulfonic acid, 3-methylpentanesulfonic acid, 4-methylpentanesulfonic acid, 1,1-dimethylbutanesulfonic acid, 1,2-dimethylbutanesulfonic acid, 1,3-dimethylbutanesulfonic acid, 2,2-dimethylbutanesulfonic acid, 2,3-dimethylbutanesulfonic acid, 3,3-dimethylbutanesulfonic acid, 1-ethylbutanesulfonic acid, 2-ethylbutanesulfonic acid, 1,1, 2-trimethylpropanesulfonic acid, 1,2,2-trimethylpropanesulfonic acid, 1-ethyl- 1-methylpropanesulfonic acid and 1-ethyl-2-methylpropanesulfonic acid, or $C_1$-$C_{20}$-phosphonic acids, in particular $C_1$-$C_6$-alkanephosphonic acids, such as methanephosphonic acid, ethanephosphonic acid, propanephosphonic acid, 1-methylethanephosphonic acid, butanephosphonic acid, 1-methylpropanephosphonic acid, 2-methylpropanephosphonic acid, 1,1-dimethylethanephosphonic acid, pentanephosphonic acid, 1-methylbutanephosphonic acid, 2-methylbutanephosphonic acid, 3-methylbutanephosphonic acid, 1,1-dimethylpropanephosphonic acid, 1,2-dimethylpropanephosphonic acid, 2,2-dimethylpropanephosphonic acid and 1-ethylpropanephosphonic acid, benzenephosphonic acid and corresponding derivatives substituted in the phenyl nucleus, hexanephosphonic acid, 1-methylpentanephosphonic acid, 2-methylpentanephosphonic acid, 3-methylpentanephosphonic acid, 4-methylpentanephosphonic acid, 1,1-dimethylbutanephosphonic acid, 1,2-dimethylbutanephosphonic acid, 1,3-dimethylbutanephosphonic acid, 2,2-dimethylbutanephosphonic acid, 2,3-dimethylbutanephosphonic acid, 3,3-dimethylbutanephosphonic acid, 1-ethylbutanephosphonic acid, 2-ethylbutanephosphonic acid, 1,1,2-trimethylpropanephosphonic acid, 1,2,2-trimethylpropanephosphonic acid, 1-ethyl-1-methylpropanephosphonic acid and 1-ethyl- 2-methylpropanephosphonic acid.

The following cyclohexenone oxime ethers Ia.01 to Ic.84 of Tables 1 and 2 are particularly preferred.

TABLE 1

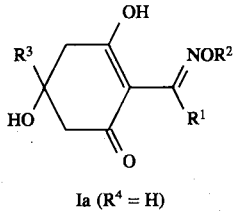

Ia (R⁴ = H)

| No. | R¹ | R² | R³ |
|---|---|---|---|
| Ia.01 | Ethyl | —CH₂CH₃ | Tetrahydropyran-4-yl |
| Ia.02 | Ethyl | —CH₂CH₃ | Tetrahydropyran-3-yl |
| Ia.03 | Ethyl | —CH₂CH₃ | 1-Methylthiocycloprop-1-yl |
| Ia.04 | Ethyl | —CH₂CH₃ | 1-Methylsulfinylcycloprop-1-yl |
| Ia.05 | Ethyl | —CH₂CH₃ | 1-Methylsulfonylcycloprop-1-yl |
| Ia.06 | Ethyl | —CH₂CH₃ | 1,3-Dimethylpyrazol-5-yl |
| Ia.07 | Ethyl | —CH₂CH₃ | 3-Isopropylisoxazol-5-yl |
| Ia.08 | Ethyl | —CH₂CH₃ | 2,4,6-Trimethylphenyl |
| Ia.09 | Ethyl | trans-CH₂CH=CHCl | Tetrahydropyran-4-yl |
| Ia.10 | Ethyl | trans-CH₂CH=CHCl | Tetrahydropyran-3-yl |
| Ia.11 | Ethyl | trans-CH₂CH=CHCl | 1-Methylthiocycloprop-1-yl |
| Ia.12 | Ethyl | trans-CH₂CH=CHCl | 1-Methylsulfinylcycloprop-1-yl |
| Ia.13 | Ethyl | trans-CH₂CH=CHCl | 1-Methylsulfonylcycloprop-1-yl |
| Ia.14 | Ethyl | trans-CH₂CH=CHCl | 1,3-Dimethylpyrazol-5-yl |
| Ia.15 | Ethyl | trans-CH₂CH=CHCl | 3-Isopropylisoxazol-5-yl |
| Ia.16 | Ethyl | trans-CH₂CH=CHCl | 2,4,6-Trimethylphenyl |
| Ia.17 | Propyl | —CH₂CH₃ | Tetrahydropyran-4-yl |
| Ia.18 | Propyl | —CH₂CH₃ | Tetrahydropyran-3-yl |
| Ia.19 | Propyl | —CH₂CH₃ | 1-Methylthiocycloprop-1-yl |
| Ia.20 | Propyl | —CH₂CH₃ | 1-Methylsulfinylcycloprop-1-yl |
| Ia.21 | Propyl | —CH₂CH₃ | 1-Methylsulfonylcycloprop-1-yl |
| Ia.22 | Propyl | —CH₂CH₃ | 1,3-Dimethylpyrazol-5-yl |
| Ia.23 | Propyl | —CH₂CH₃ | 3-Isopropylisoxazol-5-yl |
| Ia.24 | Propyl | —CH₂CH₃ | 2,4,6-Trimethylphenyl |
| Ia.25 | Propyl | trans-CH₂CH=CHCl | Tetrahydropyran-4-yl |
| Ia.26 | Propyl | trans-CH₂CH=CHCl | Tetrahydropyran-3-yl |
| Ia.27 | Propyl | trans-CH₂CH=CHCl | 1-Methylthiopropyl-1-yl |
| Ia.28 | Propyl | trans-CH₂CH=CHCl | 1-Methylsulfinylcycloprop-1-yl |
| Ia.29 | Propyl | trans-CH₂CH=CHCl | 1-Methylsulfonylcycloprop-1-yl |
| Ia.30 | Propyl | trans-CH₂CH=CHCl | 1,3-Dimethylpyrazol-5-yl |

TABLE 1-continued

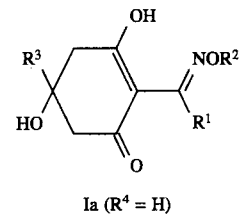

Ia (R⁴ = H)

| No. | R¹ | R² | R³ |
|---|---|---|---|
| Ia.31 | Propyl | trans-CH₂CH=CHCl | 3-Isopropylisoxazol-5-yl |
| Ia.32 | Propyl | trans-CH₂CH=CHCl | 2,4,6-Trimethylphenyl |

The cyclohexenone oxime ethers Ib.01 to Ib.32 are identical to the corresponding compounds Ia.01 to Ia.32, except for R⁴, which in this case is methyl; the cyclohexenone oxime ethers Ic.01 to Ic.32 are identical to the corresponding compounds Ia.01 to Ia 32, except for R⁴, which in this case is methylcarbonyl.

TABLE 2

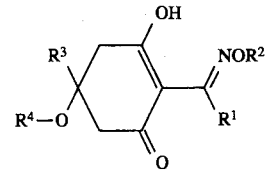

Id [R2 = trans-—CH₂CH₂CH=CH—(4-F—C₆H₅)]

| No. | R¹ | R³ | R⁴ |
|---|---|---|---|
| Id.01 | Ethyl | Tetrahydrothiopyran-3-yl | —H |
| Id.02 | Ethyl | 1-Oxo-tetrahydrothiopyran-3-yl | —H |
| Id.03 | Ethyl | 1,1-Dioxo-tetrahydrothiopyran-3-yl | —H |
| Id.04 | Ethyl | Tetrahydropyran-4-yl | —H |
| Id.05 | Ethyl | Tetrahydropyran-3-yl | —H |
| Id.06 | Ethyl | 2-Ethylthiopropyl | —H |
| Id.07 | Ethyl | 2-Ethylsulfinyl-propyl | —H |
| Id.08 | Ethyl | 2-Ethylsulfonyl-propyl | —H |
| Id.09 | Ethyl | 1-Methylthiocycloprop-1-yl | —H |
| Id.10 | Ethyl | 1-Methylsulfinylcycloprop-1-yl | —H |
| Id.11 | Ethyl | 1-Methylsulfonylcycloprop-1-yl | —H |
| Id.12 | Ethyl | 1,3-Dimethylpyrazol-5-yl | —H |
| Id.13 | Ethyl | 3-Isopropylisoxazol-5-yl | —H |
| Id.14 | Ethyl | 2,4,6-Trimethylphenyl | —H |
| Id.15 | Ethyl | Tetrahydrothiopyran-3-yl | —CH₃ |
| Id.16 | Ethyl | 1-Oxotetrahydrothiopyran-3-yl | —CH₃ |
| Id.17 | Ethyl | 1,1-Dioxo-tetrahydrothiopyran-3-yl | —CH₃ |
| Id.18 | Ethyl | Tetrahydropyran-4-yl | —CH₃ |
| Id.19 | Ethyl | Tetrahydropyran-3-yl | —CH₃ |
| Id.20 | Ethyl | 2-Ethylthiopropyl | —CH₃ |
| Id.21 | Ethyl | 2-Ethylsulfinyl-propyl | —CH₃ |
| Id.22 | Ethyl | 2-Ethylsulfonyl-propyl | —CH₃ |
| Id.23 | Ethyl | 1-Methylthiocycloprop-1-yl | —CH₃ |
| Id.24 | Ethyl | 1-Methylsulfinylcycloprop-1-yl | —CH₃ |
| Id.25 | Ethyl | 1-Methylsulfonylcycloprop-1-yl | —CH₃ |
| Id.26 | Ethyl | 1,3-Dimethylpyrazol-5-yl | —CH₃ |
| Id.27 | Ethyl | 3-Isopropylisoxazol-5-yl | —CH₃ |
| Id.28 | Ethyl | 2,4,6-Trimethylphenyl | —CH₃ |
| Id.29 | Ethyl | Tetrahydrothiopyran-3-yl | —COCH₃ |
| Id.30 | Ethyl | 1-Oxo-tetrahydrothiopyran-3-yl | —COCH₃ |
| Id.31 | Ethyl | 1,1-Dioxo-tetrahydrothiopyran-3-yl | —COCH₃ |
| Id.32 | Ethyl | Tetrahydropyran-4-yl | —COCH₃ |
| Id.33 | Ethyl | Tetrahydropyran-3-yl | —COCH₃ |
| Id.34 | Ethyl | 2-Ethylthiopropyl | —COCH₃ |

TABLE 2-continued

Id [R2 = trans-
—CH$_2$CH$_2$CH=CH—(4-F—C$_6$H$_5$)]

| No. | R$^1$ | R$^3$ | R$^4$ |
|---|---|---|---|
| Id.35 | Ethyl | 2-Ethylsulfinyl-propyl | —COCH$_3$ |
| Id.36 | Ethyl | 2-Ethylsulfonyl-propyl | —COCH$_3$ |
| Id.37 | Ethyl | 1-Methylthiocycloprop-1-yl | —COCH$_3$ |
| Id.38 | Ethyl | 1-Methylsulfinylcycloprop-1-yl | —COCH$_3$ |
| Id.39 | Ethyl | 1-Methylsulfonylcycloprop-1-yl | —COCH$_3$ |
| Id.40 | Ethyl | 1,3-Dimethylpyrazol-5-yl | —COCH$_3$ |
| Id.41 | Ethyl | 3-Isopropylisoxazol-5-yl | —COCH$_3$ |
| Id.42 | Ethyl | 2,4,6-Trimethylphenyl | —COCH$_3$ |
| Id.43 | Propyl | Tetrahydrothiopyran-3-yl | —H |
| Id.44 | Propyl | 1-Oxo-tetrahydrothiopyran-3-yl | —H |
| Id.45 | Propyl | 1,1-Dioxo-tetrahydrothiopyran-3-yl | —H |
| Id.46 | Propyl | Tetrahydropyran-4-yl | —H |
| Id.47 | Propyl | Tetrahydropyran-3-yl | —H |
| Id.48 | Propyl | 2-Ethylthiopropyl | —H |
| Id.49 | Propyl | 2-Ethylsulfinyl-propyl | —H |
| Id.50 | Propyl | 2-Ethylsulfonyl-propyl | —H |
| Id.51 | Propyl | 1-Methylthiocycloprop-1-yl | —H |
| Id.52 | Propyl | 1-Methylsulfinylcycloprop-1-yl | —H |
| Id.53 | Propyl | 1-Methylsulfonylcycloprop-1-yl | —H |
| Id.54 | Propyl | 1,3-Dimethylpyrazol-5-yl | —H |
| Id.55 | Propyl | 3-Isopropylisoxazol-5-yl | —H |
| Id.56 | Propyl | 2,4,6-Trimethylphenyl | —H |
| Id.57 | Propyl | Tetrahydrothiopyran-3-yl | —CH$_3$ |
| Id.58 | Propyl | 1-Oxo-tetrahydrothiopyran-3-yl | —CH$_3$ |
| Id.59 | Propyl | 1,1-Dioxo-tetrahydrothiopyran-3-yl | —CH$_3$ |
| Id.60 | Propyl | Tetrahydropyran-4-yl | —CH$_3$ |
| Id.61 | Propyl | Tetrahydropyran-3-yl | —CH$_3$ |
| Id.62 | Propyl | 2-Ethylthiopropyl | —CH$_3$ |
| Id.63 | Propyl | 2-Ethylsulfinyl-propyl | —CH$_3$ |
| Id.64 | Propyl | 2-Ethylsulfonyl-propyl | —CH$_3$ |
| Id.65 | Propyl | 1-Methylthiocycloprop-1-yl | —CH$_3$ |
| Id.66 | Propyl | 1-Methylsulfinylcycloprop-1-yl | —CH$_3$ |
| Id.67 | Propyl | 1-Methylsulfonylcycloprop-1-yl | —CH$_3$ |
| Id.68 | Propyl | 1,3-Dimethylpyrazol-5-yl | —CH$_3$ |
| Id.69 | Propyl | 3-Isopropylisoxazol-5-yl- | —CH$_3$ |
| Id.70 | Propyl | 2,4,6-Trimethylphenyl | —CH$_3$ |
| Id.71 | Propyl | Tetrahydrothiopyran-3-yl | —COCH$_3$ |
| Id.72 | Propyl | 1-Oxo-tetrahydrothiopyran-3-yl | —COCH$_3$ |
| Id.73 | Propyl | 1,1-Dioxo-tetrahydrothiopyran-3-yl | —COCH$_3$ |
| Id.74 | Propyl | Tetrahydropyran-4-yl | —COCH$_3$ |
| Id.75 | Propyl | Tetrahydropyran-3-yl | —COCH$_3$ |
| Id.76 | Propyl | 2-Ethylthiopropyl | —COCH$_3$ |
| Id.77 | Propyl | 2-Ethylsulfinyl-propyl | —COCH$_3$ |
| Id.78 | Propyl | 2-Ethylsulfonyl-propyl | —COCH$_3$ |
| Id.79 | Propyl | 1-Methylthiocycloprop-1-yl | —COCH$_3$ |
| Id.80 | Propyl | 1-Methylsulfinylcycloprop-1-yl | —COCH$_3$ |
| Id.81 | Propyl | 1-Methylsulfonylcycloprop-1-yl | —COCH$_3$ |
| Id.82 | Propyl | 1,3-Dimethylpyrazol-5-yl | —COCH$_3$ |
| Id.83 | Propyl | 3-Isopropylisoxazol-5-yl | —COCH$_3$ |
| Id.84 | Propyl | 2,4,6-Trimethylphenyl | —COCH$_3$ |

The cyclohexenone oxime ethers Ie.01 to Ie.84 are identical to the corresponding compounds Id.01 to Id.84, except for R$^2$, which in this case is —CH$_2$CH$_2$CH$_2$CH$_2$—(4—F—C$_6$H$_4$);

the cyclohexenone oxime ethers If.01 to If.84 are identical to the corresponding compounds Id.01 to Id.84, except for R$^2$, which in this case is —CH$_2$CH(CH$_3$)—O—(4—Cl—C$_6$H$_4$);

the cyclohexenone oxime ether Ig.01 to Ig.84 are identical to the corresponding compounds Id.01 to Id.84, except for R$^2$, which in this case is —CH$_2$CH$_2$—O—(2,4—F$_2$—C$_6$H$_3$);

the cyclohexenone oxime ether Ih.01 to Ih.84 are identical to the corresponding compounds Id.01 to Id.84 except for R$^2$, which in this case is —CH$_2$—(5-Cl-thiene-2-yl);

the cyclohexenone oxime ether Ii.01 to Ii.84 are identical to the corresponding compounds Id.01 to Id.84, except for R$^2$, which in this case is —CH$_2$CH$_2$CH$_2$CH$_2$—(thiene-2-yl).

The cyclohexenone oxime ether I and their salts and esters are suitable (both as isomeric mixtures and in the form of the pure isomers) as herbicides, in particular for controlling plant species from the family consisting of the grasses (Gramineae).

In general, they are tolerated and therefore selective in broad-leafed crops and in monocotyledin plants which do not belong to the Gramineae. Some of the novel cyclohexenone oxime ethers I are also suitable for selectively controlling undesirable grasses in gramineous crops.

The cyclohexenone oxime ethers I and the herbicides containing them can be applied, for example, in the form of directly sprayable aqueous solutions, powders, suspensions, including highly concentrated aqueous, oily or other suspensions or dispersions, emulsions, oil dispersions, pastes, dusting agents, broadcasting agents or granules, by spraying, nebulizing, dusting, broadcasting or pouring. The application forms depend on intended uses; they should in any case ensure as far as possible very fine distribution of the novel active ingredients. The compounds I are suitable in general for the preparation of directly sprayable solutions, emulsions, pastes or oil dispersions. Suitable inert additives are mineral oil fractions having a medium to high boiling point, such as kerosine or diesel oil, and coal tar oils and oils of vegetable or animal origin, aliphatic, cyclic and aromatic hydrocarbons, for example paraffin, tetrahydronaphthaline, alkylated naphthaline or their derivatives, alkylated benzenes or their derivatives, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water dispersible granules by adding water. For the preparation of emulsions, pastes or oil dispersions, the substances, as such or dissolved in an oil or solvent, can be homogenized in water by means of wetting agents, adherents, dispersants or emulsifiers. However, it is also possible to prepare concentrates which consist of active ingredient, wetting agents, adherents, dispersants or emulsifiers and possibly solvent or oil and which are suitable for dilution with water.

Suitable surfactants are the alkali metal, alkaline-earth metal and ammonium salts of aromatic sulfonic acids, for example ligninsulfonic, phenolsulfonic, naphthalenesulfonic and dibutylnaphthalene sulfonic acid, and of fatty acids, alkyl sulfonates and alkylaryl sulfonates, alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenol polyglycol ether, tributylphenyl polyglycol ether, alkylaryl polyether alcohols, isotridecyl alcohol, fatty alcohol ethylene oxide condensates, ethoxylated castor oil, polyoxyethylene alkyl ether or polyoxypropylene, lauryl alcohol polyglycol ether acetate, sorbitol ester, lignin sulfite waste liquors or methylcellulose.

Powders, broadcasting agents and dusting agents can be prepared by mixing or milling the active ingredients together with a solid carrier.

Granules, for example coated, impregnated and homogenous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate, ureas and vegetable products, such as grain flour, bark meal, wood meal and nutshell meal, cellulose powders or other solid carriers.

The formulations contain in general from 0.01 to 95, preferably from 0.5 to 90, parts by weight of active ingredient. The active ingredients are used here in a purity of from 90 to 100%, preferably from 95 to 100% (according to NMR spectrum).

The compounds I according to the invention can be formulated, for example, as follows:

I 20 parts by weight of compound No. 1.26 are dissolved in a mixture of 80 parts by weight of alkylated benzene, 10 parts by weight of the adduct of 8 to 10 mol of ethylene oxide with 1 mol of N-monoethanolamide and 5 parts by weight of the adduct of 40 mol ethylene oxide with 1 mol of castor oil. By pouring the solution into 100 000 parts by weight of water and finely distributing it therein, an aqueous dispersion which contains from 0.02% by weight of the active ingredient is obtained.

II 20 parts by weight of compound No. 1.04 are dissolved in a mixture which consists of 40 parts by weight of cyclohexanone, 30 parts by weight of isobutanol, 20 parts of weight of the adduct of 7 mol of ethylene oxide with 1 mol of isooctylphenyl and 10 parts by weight of the adduct of 40 mol of ethylene oxide with 1 mol of castor oil. By pouring the solution into 100 000 parts by weight of water and finely distributing it therein, an aqueous dispersion which contains 0.02% by weight of the active ingredient is obtained.

III 20 parts by weight of active ingredient No. 1.06 are dissolved in a mixture which consists of 25 parts by weight of cyclohexanone, 65 parts by weight of a mineral oil fraction boiling within the range 210° to 280° C. and 10 parts by weight of the adduct of 40 mol of ethylene oxide with 1 mol of castor oil. By pouring the solution into 100 000 parts by weight of water and finely distributing it therein, an aqueous dispersion which contains from 0.02% by weight of the active ingredient is obtained.

IV 20 parts by weight of active ingredient No. 1.25 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20 000 parts by weight of water, a spray liquor which contains 0.1% by weight of active ingredient is obtained.

V 3 parts by weight of active ingredient No. 1.24 are mixed with 97 parts by weight of finely divided kaolin. A dusting agent which contains 3% by weight of active ingredient is obtained in this manner.

VI 20 parts by weight of active ingredient No. 1.18 are thoroughly mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

The herbicides or the active ingredients may be applied by the pre-emergence or post-emergence method. If the active ingredients are less well tolerated by certain crops, it is possible to use application methods in which herbicides are sprayed with the aid of the sprayers in such a way that the leaves of the sensitive crops are as far as possible not affected while the active ingredients reach the leaves of undesirable plants growing underneath or the uncovered soil surface (post-directed, lay-by). The application rates of active ingredient are from 0.001 to 3.0, preferably from 0.01 to 1.0, kg/ha of active substance (a.s.), depending on the aim of control, season, the target plants and the stage of growth.

In view of the versatility of the application methods, the cyclohexenone oxime ether I or agents containing them can also be used in a further number of crops for eliminating undesirable plants. For example, the following crops are suitable: *Allium cepa, Ananas comosus, Arachis hypogaea, Asparagus officinalis, Beta vulgaris spp. altissima, Beta vulgaris spp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis Guineensis, Fragaria vesca, Glycine max, Gossypium hirsutum (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicaco sativa, Musa spp., Nicotiana tabacum (N. rustica), Olea europaea, Oryza satira, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare),* Theobroma cacao, Trifolium pratense, Triticum aestivum, Triticum durum, Vicia faba, Vitis vinifera, Zea mays.

In order to broaden the action spectrum and to achieve synergistic effects, the cyclohexenone oxime ether I can be mixed with, and applied together with, a large number of members of other groups of herbicidal or growth-regulating active ingredients. Examples of suitable components of the mixture are diazines, 4H-3, 1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uraciles, benzofuran derivatives, cyclohexane- 1,3-dione derivatives, which, for example, carry a carboxyl or carbimino group in the 2-position, quinoline-carboxylic acid derivatives, imidazolinones, sulfonamides, sulfonylureas, aryloxyphenoxypropionic acid, heteroaryloxyphenoxypropionic acid and the salts, esters and amides thereof and others.

It may furthermore be useful to apply the compounds I, alone or in combination with other herbicides, also mixed together with further crop protection agents, for example, with pesticides or agents for controlling phytopathogenic fungi or bacteria. The miscibility with mineral salt solutions which are used for eliminating nutrient and trace element deficiencies is also of interest. Nonphytotoxic oils and oil concentrates may also be added.

SYNTHESIS EXAMPLES

The synthesis methods described in the examples shown below were used, with modification of the starting materials, for the preparation of further cyclohexenone oxime ethers of the formula I. The compounds thus obtained are shown in the subsequent tables together with physical data.

EXEMPLARY PREPARATION METHOD 3,5-dihydroxy-2-propionyl-5-(2H-tetrahydropyran-4-yl)-2-cyclohexen-1-one (No. IV.1)

46.8 g (0.3 mol) of 3-acetyl-2,4-hexanedione were added dropwise at (−70)° C. to a solution of 0.9 mol of lithium diisopropylamide (prepared from 90.9 g of diisopropylamine and 384 g of a 15% solution of n-butyllithium in hexane) in 800 ml of THF under nitrogen. The stirring was carried out for a further 1.5 hours at (−70)° C., the reaction mixture was left to warm to room temperature and 44.6 g (0.3 mol) of 2H-tetrahydropyran-4-carbonyl chloride were then added dropwise at (−70)° C. Stirring was carried out for a further 1.5 hours at (−70)° C. and the mixture was left overnight to warm up to about 20° C. The reaction mixture was then stirred into 800 ml of iced water and brought to a pH of 5 (pH meter) with concentrated hydrochloric acid at below 15° C. The organic phase was separated off and the aqueous phase was extracted twice more with MTB. The combined organic phases were dried over $Na_2SO_4$ and evaporated down under reduced pressure..The dark oil obtained was stirred in 300 ml of diisopropyl ether and the precipitate obtained was separated off, washed with a little diisopropyl ether and dried.

Yield: 7.9 g (10%) of a pale yellow solid; m.p. 148°–153° C.

$^1$H—NMR (200 MHz, in $CDCl_3$): δ [ppm]=1.15 (t,3H), 1.30–1.80 (m,5H), 2.50–2.80 (m,4H), 3.10 (q,2H), 3.35 (m,2H), 4.05 (m,2H), 4.50 (bs,1H), 18.20 (bs,1H).

2-[1-[[(E)-3-Chloro-2-propen-1-yloxy]imino]propyl]-3,5-dihydroxy- 5-(2H-tetrahydropyran-4-yl)-2-cyclohexen-1-one (I.24)

6.0 g (0.022 mol) of cyclohexenone (No. IV.1), 3.6 g (0.025 mol) of O-[(E)-3-chloro-2-propen-1-yl]hydroxylamine hydrochloride and 2.1 g (0.025 mol) of $NaHCO_3$ in 100 ml of methanol were stirred for 24 hours at from about from 20° to 25° C. The mixture was evaporated under reduced pressure, the residue was taken up in water and the solution was acidified with 10% strength hydrochloric acid and extracted with methylene chloride. The organic phase was separated off, dried over sodium sulfate and evaporated down under reduced pressure.

Yield: 7.9 g (100%) of a pale brown solid; mp. 129°–132° C.

$^1$H—NMR (200 MHz, in $CDCl_3$): δ [ppm]=1.15 (t,3H), 1.30–1.80 (m,5H), 2.00 (bs,1H), 2.50–2.80 (m,4H), 2.90 (q,2H), 3.40 (m,2H), 4.05 (m,2H), 4.50 (d,2H), 6.10 (m, 1H), 6.35 (d, 1H), 14.50 (bs,1H).

[Abbreviations: THF=tetrahydrofuran; MTB=Methyl tert-butyl ether]

TABLE 3

| No. | $R^1$ | $R^3$ | Physical data ($^1$H-NMR [ppm]; IR [cm$^{-1}$]; M.p. |
|---|---|---|---|
| IV.1 | Ethyl | tetrahydropyran-4-yl (O) | 148–153° C. |
| IV.2 | n-Propyl | tetrahydropyran-4-yl (O) | 176–177° C. |
| IV.3 | Ethyl | tetrahydrothiopyran-4-yl (S) | 159–162° C. |
| IV.4 | n-Propyl | tetrahydrothiopyran-4-yl (S) | 142–144° C. |
| IV.5 | n-Propyl | $(CH_3)_2CH-C(=N-O-CH(CH_3)_2)-$ | 124–125° C. |
| IV.6 | n-Propyl | 2-nitrophenyl | 166–167° C. |
| IV.7 | n-Propyl | 2,4-dichlorophenyl | 147–151° C. |
| IV.8 | n-Propyl | cyclohexyl | 155° C. |
| IV.9 | n-Propyl | tetrahydropyran-4-yl (O) | 110–112° C. |

TABLE 3-continued

Structure IV:

$$\text{cyclohexanone with } R^3, \text{OH at one carbon, OH and } C(=O)R^1 \text{ substituents}$$

| No. | R¹ | R³ | Physical data (¹H-NMR [ppm]; IR [cm⁻¹]; M.p. |
|---|---|---|---|
| IV.10 | Methyl | tetrahydropyran-3-yl (O) | 105–110° C. |
| IV.11 | Methyl | tetrahydrothiopyran-3-yl (S) | 118–120° C. |
| IV.12 | Ethyl | tetrahydropyran-3-yl (O) | 80–84° C. |
| IV.13 | n-Propyl | cyclopropyl | 0,50(m, 4H), 1.00 (t, 3H), 1,05(m, 1H), 1,65(m, 2H), 2,55(m, 2H), 2,80 (m, 2H), 3,00(m, 2H) |

TABLE 4

Structure I (where R⁴ = H):

cyclohexanone with $R^3$, $R^4O$ substituents, OH, and $C(=NOR^2)R^1$ group

| No. | R¹ | R² | R³ | Physical data (¹H-NMR [ppm]; IR [cm⁻¹]; M.p.) |
|---|---|---|---|---|
| I.01 | Ethyl | —CH₂CH₃ | tetrahydrothiopyran-3-yl | 74–90° C. |
| I.02 | Ethyl | trans-CH₂CH═CHCl | tetrahydrothiopyran-3-yl | 106–110° C. |
| I.03 | n-Propyl | —CH₂CH₃ | tetrahydrothiopyran-3-yl | 89–91° C. |
| I.04 | n-Propyl | —CH₂-(5-chlorothien-2-yl) | tetrahydrothiopyran-3-yl | 0.90(t, 3H), 5.10 (s, 2H), 6.80(m, 2H) |
| I.05 | n-Propyl | —CH₂CH(CH₃)—O—(4-chlorophenyl) | tetrahydrothiopyran-3-yl | 0.90(t, 3H), 4.15 (m, 2H), 4.60(m, 1H), 6.85(m, 2H), 7.25 (m, 2H) |
| I.06 | n-Propyl | trans-CH₂CH₂CH═CH—(4-fluorophenyl) | tetrahydrothiopyran-3-yl | 113–115° C. |

TABLE 4-continued

Structure I: cyclohexenone with OH, R³, R⁴O, =NOR², R¹ substituents (where R⁴ = H)

| No. | R¹ | R² | R³ | Physical data (¹H-NMR [ppm]; IR [cm⁻¹]; M.p.) |
|---|---|---|---|---|
| I.07 | n-Propyl | —CH₂CH₂—O—C₆H₄—Cl (4-Cl) | thian-4-yl | 0.90(t, 3H), 4.20 (m, 2H), 4.40(m, 2H), 6.85(m, 2H), 7.25 (m, 2H) |
| I.08 | n-Propyl | —CH₂CH(CH₃)—O—C₆H₃—2,4-F₂ | thian-4-yl | 0.90(t, 3H), 4.20 (m, 2H), 4.55(m, 1H), 6.70–7.10(m, 3H) |
| I.09 | n-Propyl | —CH₂CH₂CH₂CH₂—(2-thienyl) | thian-4-yl | 0.90(t, 3H), 4.00 (m, 2H), 6.80(m, 1H), 6.95(m, 1H), 7.15 (m, 1H) |
| I.10 | n-Propyl | —CH₂CH=CH₂ | thian-4-yl | — |
| I.11 | n-Propyl | —CH₂CH₂F | thian-4-yl | 100–102° C. |
| I.12 | n-Propyl | —CH₂CH₂CH₂CH₂—C₆H₄—F (4-F) | thian-4-yl | 0.90(t, 3H), 4.05 (m, 2H), 6.95(m, 2H), 7.15(m, 2H) |
| I.13 | n-Propyl | —CH₂CH₂CH₂—O—C₆H₄—F (4-F) | thian-4-yl | 0.90(t, 3H), 4.00 (t, 2H), 4.20(t, 2H), 6.80–7.00(m, 4H) |
| I.14 | n-Propyl | trans-CH₂CH=CHCH₃ | thian-4-yl | 68–70° C. |
| I.15 | n-Propyl | —CH₂CH₂—O—C₆H₃—2,4-Cl₂ | thian-4-yl | 114–116° C. |
| I.16 | n-Propyl | trans-CH₂CH=CHCl | cyclohexyl | 2.85(m, 2H), 4.50 (d, 2H), 6.10(m, 1H), 6.35(d, 1H) |
| I.17 | n-Propyl | —CH₂—(5-chloro-2-thienyl) | cyclohexyl | 99–100° C. |
| I.18 | n-Propyl | —CH₂CH(CH₃)—O—C₆H₄—Cl (4-Cl) | cyclohexyl | 2.85(m, 2H), 4.15 (m, 2H), 4.60(m, 1H), 6.85(m, 2H), 7.25 (m, 2H) |

TABLE 4-continued

(where R⁴ = H)

| No. | R¹ | R² | R³ | Physical data (¹H-NMR [ppm]; IR [cm⁻¹]; M.p.) |
|---|---|---|---|---|
| I.19 | n-Propyl | trans-CH₂CH₂CH=CH—F |  | 2.85(m, 2H), 4.15 (t, 2H), 6.10(m, 1H), 5.45(d, 1H), 7.00 (m, 2H), 7.35(m, 2H) |
| I.20 | n-Propyl | —CH₂CH₂—OCl |  | 2.85(m, 2H), 4.20 (t, 2H), 4.40(t, 2H), 6.85(m, 2H), 7.25 (m, 2H) |
| I.21 | n-Propyl | —CH₂CH(CH₃)—OF,F |  | 2.85(m, 2H), 4.20 (m, 2H), 4.55(m, 1H), 6.70–7.10(m, 3H) |
| I.22 | n-Propyl | —CH₂CH₂CH₂CH₂ |  | 2.80–3.00(m, 4H), 4.05 (m, 2H), 6.00(m, 1H), 6.95(m, 1H), 7.15 (m, 1H) |
| I.23 | n-Propyl | —CH₂CH₃ |  | 130 to 133° C. |
| I.24 | Ethyl | trans-CH₂CH=CHCl |  | 129–132° C. |
| I.25 | n-Propyl | —CH₂CH₃ | (CH₃)₂CH | 112–114° C. |
| I.26 | n-Propyl | —CH₂CH₃ | NO₂ | 150–151° C. |
| I.27 | n-Propyl | —CH₂CH₃ |  | 86–87° C. |
| I.28 | n-Propyl | —CH₂CH(CH₃)—OCl |  | 0.90(t, 3H), 4.20 (m, 2H), 4.60(m, 1H), 6.85(d, 2H), 7.20 (d, 2H) |
| I.29 | n-Propyl | —CH₂CH(CH₃)—OCl |  | 0.90(t, 3H), 4.20 (m, 2H), 4.60(m, 1H), 6.85(d, 2H), 7.20 (d, 2H) |

TABLE 4-continued $$\text{I}$$

Structure: cyclohexenone with OH, R³, R⁴O, and C(R¹)=NOR² substituents (where R⁴ = H)

| No. | R¹ | R² | R³ | Physical data (¹H-NMR [ppm]; IR [cm⁻¹]; M.p.) |
|---|---|---|---|---|
| I.30 | n-Propyl | —CH₂CH₂CH₂—O—(4-Cl-C₆H₄) | tetrahydrothiopyranyl (S) | 0.90(t, 3H), 4.05 (t, 2H), 4.25(t, 2H), 6.85(m, 2H), 7.20 (m, 2H) |
| I.31 | n-Propyl | trans-CH₂CH₂CH=CH—(4-Cl-C₆H₄) | tetrahydrothiopyranyl (S) | 0.90(t, 3H), 4.20 (t, 2H), 6.20(m, 1H), 6,40(d, 1H), 7.20 (s, 4H) |
| I.32 | n-Propyl | —CH₂CH₂CH₂CH₂—O—(4-Cl-C₆H₄) | tetrahydrothiopyranyl (S) | 0.90(t, 3H), 3.95 (m, 2H), 4.15(m, 2H), 6.80(d, 2H), 7.20 (d, 2H) |
| I.33 | n-Propyl | trans-CH₂CH=CHCl | tetrahydrothiopyranyl (S) | 0.90(t, 3H), 4.50 (d, 2H), 6.10(m, 1H), 6,30(d, 1H) |
| I.34 | n-Propyl | —CH₂CH(CH₃)—O—(2,4-diCl-C₆H₃) | tetrahydrothiopyranyl (S) | 114–116° C. |
| I.35 | n-Propyl | —CH₂CH(CH₃)—O—(4-F-C₆H₄) | tetrahydrothiopyranyl (S) | 4.20(m, 2H), 4.60 (m, 1H), 6.80–7.00 (m, 4H) |
| I.36 | n-Propyl | —CH₂CH₂CH₂CH₂—O—(4-F-C₆H₄) | tetrahydrothiopyranyl (S) | |
| I.37 | n-Propyl | —CH₂CH₂—O—CH₃ | tetrahydrothiopyranyl (S) | 0.95(t, 3H), 3.40 (s, 3H), 3.65(m, 2H), 4.20(m, 2H) |
| I.38 | n-Propyl | —CH₂CH₂—O—(4-NO₂-C₆H₄) | tetrahydrothiopyranyl (S) | 0.95(t, 3H), 4.30 (m, 2H), 4.50(m, 2H), 7.00(m, 2H), 8.20 (m, 2H) |
| I.39 | n-Propyl | —CH₂CH₂—O—CH₃ | tetrahydropyranyl (O) | 0.95(t, 3H), 3.40 (s, 3H), 3.65(m, 2H), 4.20(m, 2H) |
| I.40 | n-Propyl | —CH₂CH₂—O—(2,4-diCl-C₆H₃) | tetrahydropyranyl (O) | 83–85° C. |

TABLE 4-continued

Structure I: cyclohexane-dione with OH, R³, R⁴O substituents and C(R¹)=NOR² side chain (where R⁴ = H)

| No. | R¹ | R² | R³ | Physical data (¹H-NMR [ppm]; IR [cm⁻¹]; M.p.) |
|---|---|---|---|---|
| I.41 | n-Propyl | —CH₂CH(CH₃)—O—C₆H₄—F | tetrahydropyran-3-yl | 0.95(t, 3H), 4.15 (m, 2H), 4.55(m, 1H), 6.80–7.00(m, 4H) |
| I.42 | n-Propyl | —CH₂CH₂CH₂—O—C₆H₄—Cl | tetrahydropyran-3-yl | 70–75° C. |
| I.43 | n-Propyl | trans-CH₂CH₂CH=CH—C₆H₄—F | tetrahydropyran-3-yl | 95–100° C. |
| I.44 | n-Propyl | —CH₂CH₂—O—C₆H₅ | tetrahydropyran-3-yl | 88–90° C. |
| I.45 | n-Propyl | —CH₂CH₂CH₂—O—C₆H₄—F | tetrahydropyran-3-yl | 68–70° C. |
| I.46 | n-Propyl | —CH₂CH₂CH₂CH₂—O—C₆H₄—Cl | tetrahydropyran-3-yl | 0.95(t, 3H), 3.95 (m, 2H), 4.10(m, 2H), 6.85(d, 2H), 7.20 (d, 2H) |
| I.47 | n-Propyl | trans-CH₂CH₂CH=CH—C₆H₄—Cl | tetrahydropyran-3-yl | 69–72° C. |
| I.48 | Methyl | —CH₂CH₂—O—CH₃ | tetrahydropyran-3-yl | 2.35(s, 3H), 3.40 (s, 3H), 3.65(m, 2H), 4.20(m, 2H) |
| I.49 | Methyl | —CH₂CH(CH₃)—O—C₆H₄—F | tetrahydropyran-3-yl | 2.30(s, 3H), 4.15 (m, 2H), 4.55(m, 1H), 6.80–7.00(m, 4H) |
| I.50 | Methyl | —CH₂CH₂CH₂—O—C₆H₄—Cl | tetrahydropyran-3-yl | 75–80° C. |
| I.51 | Methyl | trans-CH₂CH₂CH=CH—C₆H₄—F | tetrahydropyran-3-yl | 123–125° C. |
| I.52 | Methyl | —CH₂CH₂—O—C₆H₅ | tetrahydropyran-3-yl | 115–117° C. |

TABLE 4-continued $$\text{structure with } R^3, R^4O, OH, NOR^2, R^1, O \text{ (where } R^4 = H\text{)}$$ I

| No. | R¹ | R² | R³ | Physical data (¹H-NMR [ppm]; IR [cm⁻¹]; M.p.) |
|---|---|---|---|---|
| I.53 | Methyl | —CH₂CH₂CH₂—O—(4-F-C₆H₄) | tetrahydropyran-yl (O) | 2.35(s, 3H), 4.05 (t, 2H), 4.25(t, 2H), 6.80(m, 2H), 6.95 (m, 2H) |
| I.54 | Methyl | —CH₂CH₂CH₂CH₂—O—(4-Cl-C₆H₄) | tetrahydropyran-yl (O) | 2.40(s, 3H), 3.95 (m, 2H), 4.15(m, 2H), 6.85(m, 2H), 7.20 (m, 2H) |
| I.55 | methyl | —CH₂CH₂—O—CH₃ | tetrahydrothiopyran-yl (S) | 2.40(s, 3H), 3.40 (s, 3H), 3.65(m, 2H), 4.20(m, 2H) |
| I.56 | Methyl | —CH₂CH—O—(2,4-Cl₂-C₆H₃) | tetrahydrothiopyran-yl (S) | 170–173° C. |
| I.57 | Methyl | —CH₂CH(CH₃)—O—(4-F-C₆H₄) | tetrahydrothiopyran-yl (S) | 98–100° C. |
| I.58 | Methyl | —CH₂CH₂CH₂—O—(4-Cl-C₆H₄) | tetrahydrothiopyran-yl (S) | 133–136° C. |
| I.59 | Methyl | trans-CH₂CH₂CH=CH—(4-F-C₆H₄) | tetrahydrothiopyran-yl (S) | 130–131° C. |
| I.60 | Methyl | —CH₂CH₂—O—C₆H₅ | tetrahydrothiopyran-yl (S) | 115–117° C. |
| I.61 | Methyl | —CH₂CH₂CH₂—O—(4-F-C₆H₄) | tetrahydrothiopyran-yl (S) | 110–112° C. |
| I.62 | Methyl | —CH₂CH₂CH₂CH₂—O—(4-Cl-C₆H₄) | tetrahydrothiopyran-yl (S) | 78–82° C. |
| 1.63 | Methyl | trans-CH₂CH₂CH=CH—(4-Cl-C₆H₄) | tetrahydrothiopyran-yl (S) | 160–162° C. |
| I.64 | Ethyl | —CH₂CH(CH₃)—O—(4-Cl-C₆H₄) | tetrahydrothiopyran-yl (S) | 1.10(t, 3H), 4.15 (m, 2H), 4.60(m, 1H), 6.85(d, 2H), 7.20 (d, 2H) |

TABLE 4-continued

Structure I: cyclohexenone with OH, R³, R⁴O, =NOR² substituents on C=C-C(=NOR²)R¹ system (where R⁴ = H)

| No. | R¹ | R² | R³ | Physical data (¹H-NMR [ppm]; IR [cm⁻¹]; M.p.) |
|---|---|---|---|---|
| I.65 | Ethyl | trans-CH₂CH₂CH=CH—C₆H₄—F | tetrahydrothiopyran-3-yl | 100–103° C. |
| I.66 | Ethyl | —CH₂CH₂—O—C₆H₄—Cl | tetrahydrothiopyran-3-yl | 1.10(t, 3H), 4.20 (t, 2H), 4.40(t, 2H), 6.90(m, 2H), 7.25 (m, 2H) |
| I.67 | Ethyl | —CH₂CH₂CH₂CH₂-(thiophen-2-yl) | tetrahydrothiopyran-3-yl | 81–83° C. |
| I.68 | Ethyl | —CH₂CH₂CH₂—O—C₆H₄—F | tetrahydrothiopyran-3-yl | 93–95° C. |
| I.69 | Ethyl | trans-CH₂CH=CHCH₃ | tetrahydrothiopyran-3-yl | 145–150° C. |
| I.70 | Ethyl | —CH₂CH₂—O—CH₃ | tetrahydrothiopyran-3-yl | 1.10(t, 3H), 3.40 (s, 3H), 3.65(m, 2H), 4.20(m, 2H) |
| I.71 | Ethyl | —CH₂CH₂CH₂—O—C₆H₄—Cl | tetrahydrothiopyran-3-yl | 104–106° C. |
| I.72 | Ethyl | —CH₂CH₂CH₂CH₂—O—C₆H₄—Cl | tetrahydrothiopyran-3-yl | 112–115° C. |
| I.73 | Ethyl | —CH₂CH(CH₃)—O—C₆H₄—F | tetrahydrothiopyran-3-yl | 88–90° C. |
| I.74 | Ethyl | —CH₂CH₂—O—C₆H₃(Cl)(Cl) (2,4-dichloro) | tetrahydrothiopyran-3-yl | 143–146° C. |
| I.75 | Ethyl | —CH₂CH₂F | tetrahydrothiopyran-3-yl | 98–101° C. |

TABLE 4-continued

Structure I: cyclohexenone with OH, R³, R⁴O, =NOR², R¹ substituents, where R⁴ = H

| No. | R¹ | R² | R³ | Physical data (¹H-NMR [ppm]; IR [cm⁻¹]; M.p.) |
|---|---|---|---|---|
| I.76 | Ethyl | —CH₂CH(CH₃)—O—(2,4-difluorophenyl) | tetrahydrothiopyran-4-yl (S) | 100–103° C. |
| I.77 | Ethyl | —CH₂CH₂CH₂—(4-fluorophenyl) | tetrahydrothiopyran-4-yl (S) | 1.10(t, 3H), 4.05 (t, 2H), 6.95(m, 2H), 7.15(m, 2H) |
| I.78 | Ethyl | —CH₂CH₂CH₂CH₂CH₂—O—(4-fluorophenyl) | tetrahydrothiopyran-4-yl (S) | 118–120° C. |
| I.79 | Ethyl | —CH₂CH₂CH₂—O—(4-nitrophenyl) | tetrahydrothiopyran-4-yl (S) | 134–136° C. |
| I.80 | Ethyl | trans-CH₂CH=CH—(4-chlorophenyl) | tetrahydrothiopyran-4-yl (S) | 120–123° C. |
| I.81 | Ethyl | —CH₂CH(CH₃)—O—(4-fluorophenyl) | tetrahydropyran-4-yl (O) | 50–54° C. |
| I.82 | Ethyl | —CH₂CH₂CH₂—O—(4-chlorophenyl) | tetrahydropyran-4-yl (O) | 110–115° C. |
| I.83 | Ethyl | —CH₂CH₂—O—(4-chlorophenyl) | tetrahydropyran-4-yl (O) | 108–110° C. |
| I.84 | Ethyl | —CH₂CH₂CH₂—O—(4-chlorophenyl) | tetrahydropyran-4-yl (O) | 92–94° C. |
| I.85 | n-Propyl | —CH₂CH₂—O—(4-chlorophenyl) | tetrahydropyran-4-yl (O) | 100–101° C. |
| I.86 | Methyl | —CH₂CH₂—O—(4-chlorophenyl) | tetrahydrothiopyran-4-yl (S) | 137–139° C. |
| I.87 | Methyl | —CH₂CH₂—O—(4-chlorophenyl) | tetrahydropyran-4-yl (O) | 130–132° C. |

TABLE 4-continued $$\text{[structure: cyclohexenone with } R^3, R^4O, OH, \text{NOR}^2, R^1 \text{ substituents]} \quad \text{(where } R^4 = H\text{)} \qquad I$$

| No. | $R^1$ | $R^2$ | $R^3$ | Physical data ($^1$H-NMR [ppm]; IR [cm$^{-1}$]; M.p.) |
|---|---|---|---|---|
| I.88 | n-Propyl | —CH$_2$CH$_2$—O—C$_6$H$_4$—Cl | tetrahydropyran-4-yl | 130° C. |
| I.89 | n-Propyl | —CH$_2$CH$_2$CH$_2$—O—C$_6$H$_4$—Cl | tetrahydropyran-4-yl | 91–93° C. |
| I.90 | n-Propyl | —CH(CH$_3$)CH$_2$—O—C$_6$H$_4$—F | tetrahydropyran-4-yl | 101–102° C. |
| I.91 | n-Propyl | —CH$_2$CH=CH$_2$ | tetrahydropyran-4-yl | 109–110° C. |
| I.92 | n-Propyl | —CH$_2$CH$_2$CH$_2$—C$_6$H$_4$—F | tetrahydropyran-4-yl | 88–90° C. |
| I.93 | n-Propyl | —CH$_2$CH$_2$—O—CH$_3$ | tetrahydropyran-4-yl | 76–77° C. |
| I.94 | n-Propyl | —CH$_2$CH$_2$CH$_2$—O—C$_6$H$_4$—NO$_2$ | tetrahydropyran-4-yl | 110–112° C. |
| I.95 | n-Propyl | trans-CH$_2$CH$_2$CH=CH—C$_6$H$_4$—F | tetrahydropyran-4-yl | 109–110° C. |
| I.96 | n-Propyl | —CH$_2$CH$_2$—F | tetrahydropyran-4-yl | 108–110° C. |
| I.97 | n-Propyl | trans-CH$_2$CH=CHCH$_3$ | tetrahydropyran-4-yl | 101–102° C. |
| I.98 | n-Propyl | —CH$_2$CH$_2$CH$_2$CH$_2$CH$_2$—O—C$_6$H$_4$—F | tetrahydropyran-4-yl | 81–82° C. |
| I.99 | n-Propyl | —CH(CH$_3$)CH$_2$—O—C$_6$H$_4$—Cl | tetrahydropyran-4-yl | 92–93° C. |

TABLE 4-continued

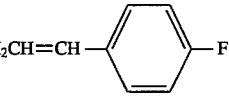

(where R⁴ = H)

| No. | R¹ | R² | R³ | Physical data ($^1$H-NMR [ppm]; IR [cm$^{-1}$]; M.p.) |
|---|---|---|---|---|
| I.100 | Ethyl | trans-CH₂CH₂CH=CH—⟨C₆H₄⟩—F |  | 1.10(t, 3H), 4.20 (t, 2H), 6.10(m, 1H), 6.45(d, 1H), 7.00 (m, 2H), 7.30(m, 2H) |
| I.101 | Ethyl | —CH₂CH₂—O—⟨C₆H₅⟩ | 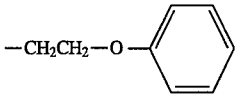 | 1.10(t, 3H), 4.20 (m, 2H), 4.40(m, 2H), 6.95(m, 3H), 7.30 (m, 2H) |
| I.102 (Benzoate) | Methyl | —CH₂CH(CH₃)—O—⟨C₆H₄⟩—F |  | 1.95(s, 3H), 3.85 (m, 1H), 4.05(m, 1H), 4.25(m, 1H), 6.75 (m, 2H), 6.90(m, 2H), 7.45(m, 2H), 7.60 (m, 1H), 8.00(m, 2H), |
| I.103 | n-Propyl | —CH₂CH₂CH₂—O—⟨C₆H₄⟩—F | 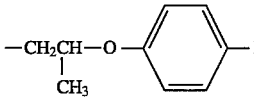 | 87–89° C. |
| I.104 | n-Propyl | —CH₂CH₂CH₂CH₂—O—⟨C₆H₄⟩—Cl |  | 94–96° C. |
| I.105 | n-Propyl | —CH₂*CH(CH₃)—O—⟨C₆H₃⟩(F)(F) (*R-Konfiguration) | 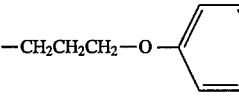 | 115–116° C. [α]$_{25}^D$ = –15.1, c = 1.0, CH₃OH |
| I.106 | n-Propyl | trans-CH₂CH=CH—⟨C₆H₄⟩—Cl |  | 139–141° C. |
| I.107 | n-Propyl | —CH₂CH(CH₃)—O—⟨C₆H₄⟩—Cl | 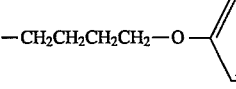 | 0.50(m, 4H), 4.20 (m, 2H), 4.60(m, 1H), 6.85(m, 2H), 7.20 (m, 2H) |
| I.108 | n-Propyl | trans-CH₂CH=CHCl |  | 84–86° C. |
| I.109 | n-Propyl | trans-CH₂CH₂CH=CH—⟨C₆H₄⟩—F | 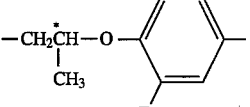 | 0.45(m, 4H), 4.15 (t, 2H), 6.10(m, 1H), 6.45(m, 1H), 7.00 (m, 2H), 7.30(m, 2H) |
| I.110 (Potassium salt) | Ethyl | trans-CH₂CH=CHCl |  | 0.90(t, 3H), 4.40 (d, 2H), 6.10(m, 1H), 6.50(d, 1H) |
| I.111 (Sodium salt) | Ethyl | trans-CH₂CH=CHCl | 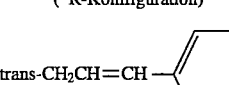 | |

TABLE 4-continued

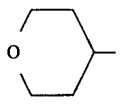

(where R⁴ = H)

| No. | R¹ | R² | R³ | Physical data (¹H-NMR [ppm]; IR [cm⁻¹]; M.p.) |
|---|---|---|---|---|
| I.112 (Lithium salt) | Ethyl | trans-CH₂CH=CHCl | 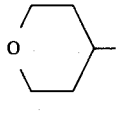 | 1.15(t, 3H), 4.55 (d, 2H), 6.10(m, 1H), 6.35(d, 1H) |
| I.113 (Benzyltri-methyl-ammonium salt) | Ethyl | trans-CH₂CH=CHCl | 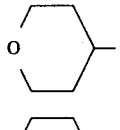 | 1.00(t, 3H), 3.15 (s, 9H), 4.40(d, 2H), 4.60(s, 2H), 7.50 (s, 5H) |
| I.114 (Tetrabutyl-ammonium salt) | Ethyl | trans-CH₂CH=CHCl | 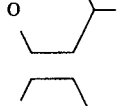 | 4.55(d, 2H), 6.10 (m, 1H), 6.35(d, 1H) |
| I.115 (Magnesium salt) | Ethyl | trans-CH₂CH=CHCl | 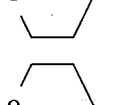 | |
| I.116 (Calcium salt) | Ethyl | trans-CH₂CH=CHCl | 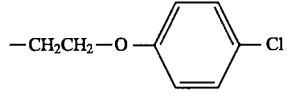 | 1.10(t, 3H), 4.55 (d, 2H), 6.10(m, 1H), 6.35(d, 1H) |
| I.117 | Ethyl | 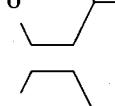 | 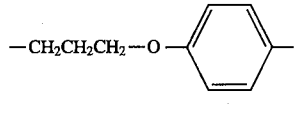 | 139–141° C. |
| I.118 | Ethyl | 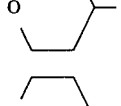 | 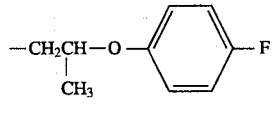 | 114–116° C. |
| I.119 | Ethyl | 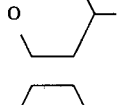 | 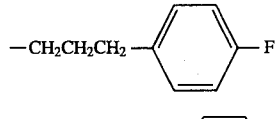 | 128–130° C. |
| I.120 | Ethyl | 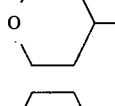 | 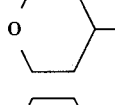 | 110–112° C. |
| I.121 | Ethyl | trans-CH₂CH=CH—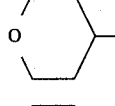—Cl | 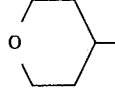 | 132–141° C. |
| I.122 | Ethyl | —CH₂CH=CH₂ | 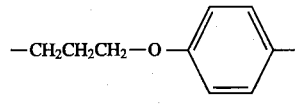 | 132–135° C. |
| I.123 | Ethyl | —CH₂CH₂—O—CH₃ | 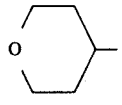 | 110–112° C. |
| I.124 | Ethyl | —CH₂CH₂CH₂—O—⌬—NO₂ | ⌬ | 125–128° C. |

TABLE 4-continued

Structure I: cyclohexenone with OH, R³, R⁴O substituents and =NOR² oxime group with R¹ (where R⁴ = H)

| No. | R¹ | R² | R³ | Physical data (¹H-NMR [ppm]; IR [cm⁻¹]; M.p.) |
|---|---|---|---|---|
| I.125 | Ethyl | trans-CH₂CH₂CH=CH—C₆H₄—F | tetrahydropyran-4-yl (O) | 138–140° C. |
| I.126 | Ethyl | —CH₂CH=F | tetrahydropyran-4-yl (O) | 150–152° C. |
| I.127 | Ethyl | trans-CH₂CH=CHCH₃ | tetrahydropyran-4-yl (O) | 148–150° C. |
| I.128 | Ethyl | —CH₂CH(CH₃)—O—C₆H₄—Cl | tetrahydropyran-4-yl (O) | 1.10(t, 3H), 4.15 (m, 2H), 4.60(m, 1H), 6.85(m, 2H), 7.20 (m, 2H) |
| I.129 (Benzoate) | Ethyl | trans-CH₂CH=CHCl | tetrahydropyran-4-yl (O) | 87–89° C. |
| I.130 (4-Chloro-benzoate) | Ethyl | trans-CH₂CH=CHCl | tetrahydropyran-4-yl (O) | 72–75° C. |
| I.131 (4-Fluoro-benzoate) | Ethyl | trans-CH₂CH=CHCl | tetrahydropyran-4-yl (O) | 102–105° C. |
| I.132 (3,5-Dimethoxy-benzoate) | Ethyl | trans-CH₂CH=CHCl | tetrahydropyran-4-yl (O) | 1.00(t, 3H), 3.80 (s, 6H), 4.40(d, 2H), 5.90(m, 1H), 6.10 (d, 1H), 6.70(m, 1H), 7.15(m, 2H) |
| I.133 | Ethyl | —CH₂CH₂CH₂—O—C₆H₄—F | tetrahydropyran-4-yl (O) | 1.10(t, 3H), 4.25 (t, 2H), 6.80–7.05 (m, 4H) |
| I.134 (4-Nitro-benzoate) | Ethyl | trans-CH₂CH=CHCl | tetrahydropyran-4-yl (O) | 93–95° C. |
| I.135 (4-Chloro-benzoate) | n-Propyl | —CH₂CH₃ | tetrahydrothiopyran-4-yl (S) | 0.90(t, 3H), 3.90 (q, 2H), 7.50(d, 2H), 7.95(d, 2H) |
| I.136 (4-Nitro-benzoate) | n-Propyl | —CH₂CH₃ | tetrahydrothiopyran-4-yl (S) | 0.90(t, 3H), 3.90 (q, 2H), 8.20–8.40 (m, 4H) |

TABLE 4-continued

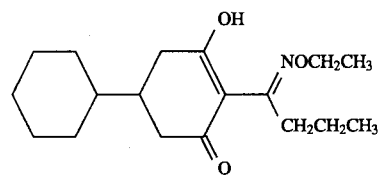
(where $R^4 = H$)

| No. | $R^1$ | $R^2$ | $R^3$ | Physical data ($^1$H-NMR [ppm]; IR [cm$^{-1}$]; M.p.) |
|---|---|---|---|---|
| I.137 (4-Fluoro-benzoate) | n-Propyl | $-CH_2CH_3$ | (thiane ring) | 0.90(t, 3H), 3.90 (q, 2H), 7.20(m, 2H), 8.05(m, 2H) |
| I.138 (3,5-Dimethoxy-benzoate) | n-Propyl | $-CH_2CH_3$ | (thiane ring) | 0.90(t, 3H), 3.80 (s, 6H), 3.90(q, 2H), 6.70(m, 1H), 7.15 (m, 2H) |
| I.139 (Benzoate) | n-Propyl | $-CH_2CH_3$ | (thiane ring) | 0.90(t, 3H), 3.90 (q, 2H), 7.40–7.70 (m, 3H), 8.05(d, 2H) |

USE EXAMPLES (HERBICIDAL ACTIVITY)

The herbicidal action of the cyclohexenone oxime ethers I could be demonstrated by greenhouse experiments:

The culture vessels used were plastic flower pots containing loamy sand with about 3.0% by weight of humus as a substrate. The seeds of the test plants were sown separately according to species.

In the pre-emergence treatment, the active ingredients suspended or emulsified in water were applied directly after sowing, by means of finely distributing nozzles. The vessels were lightly sprinkler-irrigated in order to promote germination and growth and were then covered with transparent plastic covers until the plants had begun to grow. This covering ensured more uniform germination of the test plants, unless they had been adversely affected by the active ingredients.

For the postemergence treatment, the test plants were grown to a height of growth of from 3 to 15 cm, depending on the form of growth, before being treated with the active ingredients suspended or emulsified in water. The test plants were either sown and grown directly in the test vessels in which they were treated, or they were grown separately as seedlings and transplanted into the test vessels a few days before the treatment with the active ingredient preparations.

The plants were kept at from 10° to 25° C. or from 20° to 35° C., according to species. The experimental period extended over 2 to 4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage or normal course of growth.

The comparative agent used was the compound A disclosed in JP-A 1979/019,945:

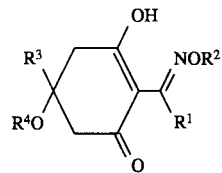

The application rate for the postemergence treatment was 0.125 and 0.06 kg/ha a.i. (active ingredient).

The plants used in the following greenhouse methods consisted of the following species:

| Botanical name | Common name |
|---|---|
| Avena fatua | wild oats |
| Bromus inermis | smooth brome |
| Digitaria sanguinalis | large crabgrass |
| Echinochloa crus-galli | barnyardgrass |
| Setaria italica | foxtail millet |
| Sorghum halpense | johnsongrass |
| Triticum aestivum | winter wheat |

The result showed that compound No. I.27 more readily controls undesirable weeds and at the same time is better tolerated by the crop than the known active ingredient A.

We claim:

1. Cyclohexenone oxime ethers of the formula I

I in which the substituents have the following meaning:

$R^1$ is $C_1$-$C_6$-alkyl;

$R^2$ is $C_1$-$C_{10}$-alkyl, $C_1$-$C_{10}$-haloalkyl, $C_3$-$C_{10}$-alkenyl, $C_3$-$C_{10}$-haloalkenyl, $C_3$-$C_{10}$-alkynyl or $C_3$-$C_{10}$-haloalkynyl;

—$A^1$—O—N=CH—Ph or —$A^2$—W; where $A^1$ is $C_2$-$C_4$-alkylene which may carry from one to three $C_1$-$C_3$-alkyl groups;

Ph is phenyl which may be unsubstituted or may carry from one to three radicals selected from a group consisting of nitro, cyano, halogen, $C_1$-$C_4$-alkyl and $C_1$-$C_4$-haloalkyl;

$A^2$ is $C_1$-$C_6$-alkylene, $C_3$-$C_6$-alkenylene or $C_3$-$C_6$-alkynylene, where these radicals may in each case carry from one to three of the following groups: halogen and/or $C_1$-$C_3$-alkyl;

or is $C_2$-$C_5$-alkyleneoxy, $C_2$-$C_5$-alkenyleneoxy or $C_2$-$C_4$-alkyleneoxy-$C_1$-$C_3$-alkylene having a total of from three to five carbon atoms, where these radicals may in each case carry from one to three $C_1$-$C_3$-alkyl groups;

W is phenyl, pyridyl or thienyl, where the rings may in each case be unsubstituted or may carry from one to three of the following radicals: nitro, cyano, halogen, $C_1$-$C_4$-alkyl and/or $C_1$-$C_4$-haloalkyl;

$R^3$ is $C_1$-$C_6$-alkyl which carries one of the following groups: $C_1$-$C_4$-alkoxy or $C_1$-$C_4$-alkylthio;

$C_3$-$C_7$-cycloalkyl or $C_5$-$C_7$-cycloalkenyl, where these radicals may be unsubstituted or may carry from one to three of the following substituents: hydroxyl, halogen, $C_1$-$C_4$-alkyl, $C_1$-$C_4$-haloalkyl, $C_1$-$C_4$-alkoxy and/or $C_1$-$C_4$-alkylthio;

a 5-membered, saturated heterocyclic structure which, in addition to carbon ring members, may contain one or two oxygen and/or sulfur atoms, where this ring may be unsubstituted or may carry from one to three of the following substituents: $C_1$-$C_4$-alkyl, $C_1$-$C_4$-haloalkyl, $C_1$-$C_4$-alkoxy and/or $C_1$-$C_4$-alkylthio;

a 6-membered or 7-membered, saturated or mono- or di-unsaturated heterocyclic structure which, in addition to carbon ring members, may contain one or two oxygen and/or sulfur atoms, where this ring may be unsubstituted or may carry from one to three of the following substituents: hydroxyl, halogen, $C_1$-$C_4$-alkyl, $C_1$-$C_4$-haloalkyl, $C_1$-$C_4$-alkoxy and/or $C_1$-$C_4$-alkylthio;

a 5-membered heteroaromatic structure which, in addition to carbon ring members, contains one or two nitrogen atoms and one oxygen or one sulfur atom, where this ring may be unsubstituted or may carry from one to three of the following substituents: cyano, halogen, $C_1$-$C_4$-alkyl, $C_1$-$C_4$-haloalkyl, $C_1$-$C_4$-alkoxy, $C_1$-$C_4$-alkylthio, $C_2$-$C_6$-alkenyl, $C_2$-$C_6$-alkynyl and/or $C_1$-$C_4$-alkoxy-$C_1$-$C_4$-alkyl;

phenyl or pyridyl, where these rings may be unsubstituted or may carry from one to three of the following substituents: nitro, cyano, halogen, $C_1$-$C_4$-alkyl, $C_1$-$C_4$-haloalkyl, $C_1$-$C_4$-alkoxy, $C_1$-$C_4$-alkylthio, $C_3$-$C_6$-alkenyloxy, $C_3$-$C_6$-alkynyloxy and/or $NR^aR^b$, where $R^a$ is hydrogen, $C_1$-$C_4$-alkyl, $C_3$-$C_6$-alkenyl or $C_3$-$C_6$-alkynyl, $R^b$ is one of the radicals $R^a$ or is $C_1$-$C_6$-alkylcarbonyl or benzoyl, where the phenyl ring in turn may carry from one to three of the following radicals: nitro, cyano, halogen, $C_1$-$C_4$-alkyl, $C_1$-$C_4$-haloalkyl, $C_1$-$C_4$-alkoxy and/or $C_1$-$C_4$-alkylthio;

$R^4$ is hydrogen;

$C_1$-$C_{10}$-alkyl, $C_1$-$C_{10}$-haloalkyl, $C_3$-$C_{10}$-alkenyl, $C_3$-$C_{10}$-haloalkenyl, $C_3$-$C_{10}$-alkynyl, $C_3$-$C_{10}$-haloalkynyl, $C_1$-$C_{10}$-alkylcarbonyl or $C_1$-$C_{10}$-haloalkylcarbonyl;

benzoyl, where the phenyl ring may be unsubstituted or may carry from one to three of the following radicals: nitro, cyano, halogen, $C_1$-$C_4$-alkyl, $C_1$-$C_4$-haloalkyl, $C_1$-$C_4$-alkoxy and/or $C_1$-$C_4$-alkylthio;

—$S(=O)_2$—$R^c$, —$P(=O)(OR^d)(OR^e)$ or —$SiR^fR^gR^h$, where $R^c$, $R^d$, $R^e$, $R^f$, $R^g$ and $R^h$ independently of one another are $C_1$-$C_{10}$-alkyl, $C_1$-$C_{10}$-haloalkyl or phenyl, where the phenyl ring in turn may carry from one to three of the following radicals: nitro, cyano, halogen, $C_1$-$C_4$-alkyl, $C_1$-$C_4$-haloalkyl, $C_1$-$C_4$-alkoxy and/or $C_1$-$C_4$-alkylthio, where $R^3$ is not S-oxo-2-(ethylthio)propyl, S,S-dioxo-2-(ethylthio)propyl, S-oxotetrahydrothiopyran-3-yl or S,S-dioxotetrahydrothiopyran-3-yl when $R^1$ is propyl, $R^2$ is ethyl and $R^4$ is hydrogen, and $R^3$ is not 2-(ethylthio)propyl, S-oxo-2-(ethylthio)propyl or S,S-dioxo-2-(ethylthio)propyl when $R^1$ is ethyl, $R^2$ is 3-chloro-2-propenyl and $R^4$ is hydrogen, and $R^3$ is not S,S-dioxo-2-(ethylthio)propyl when $R^1$ is propyl, $R^2$ is ethyl and $R^4$ is methyl, and $R^3$ is not S,S-dioxo-2-(ethylthio)propyl when $R^1$ is ethyl, $R^2$ is 3-chloro-2-propenyl and $R^4$ is methyl, and the agriculturally useful salts of I and the esters of $C_1$-$C_{10}$-carboxylic acids or inorganic acids and the compounds I.

2. A process for the preparation of the compounds of the formula Ia

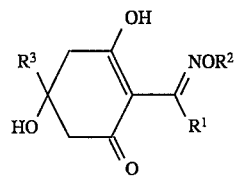

where $R^1$, $R^2$, and $R^3$ have the meanings stated in claim 1, wherein a triketone of the formula II $$(CH_3C=O)_2CH—CO—R^1 \qquad II$$

is cyclized in a conventional manner, in an inert organic solvent in the presence of a base, with an acyl halide of the formula III $$R^3—CO—Hal \qquad III$$

where Hal is a halogen atom, to give a cyclohexenone ketone of the formula IV

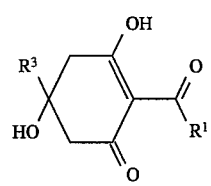

and IV is then reacted in a conventional manner, in an inert organic solvent, with a hydroxylamine of the formula V $$H_2N—OR^2 \qquad V$$

or with a corresponding hydroxylammonium salt.

3. A herbicide containing a herbicidally effective amount of at least one cyclohexenone oxime ether of the formula I as claimed in claim 1 and inert additives.

4. A method for controlling undesirable plant growth, wherein the plants and/or their habitat is or are treated with an effective amount of a cyclohexenone oxime ether of the formula I as claimed in claim 1.

5. Cyclohexenone ketones of the formula IV as claimed in claim 2.

* * * * *

UNITED STATES PATENT AND TRADEMARK OFFICE
CERTIFICATE OF CORRECTION

PATENT NO.: 5,514,642

DATED: May 7, 1996

INVENTOR(S): MISSLITZ et al.

It is certified that error appears in the above-identified patent and that said Letters Patent is hereby corrected as shown below:

On the cover page, item [57], after formula I insert the following:

--in which the substituents have the meanings defined in the specification, their preparation, agents containing them and their use.--

Signed and Sealed this

Fourth Day of March, 1997

BRUCE LEHMAN

*Attest:*

*Attesting Officer*

Commissioner of Patents and Trademarks